US008410286B2

(12) United States Patent
Bjergarde et al.

(10) Patent No.: US 8,410,286 B2
(45) Date of Patent: Apr. 2, 2013

(54) SUBSTITUTED PYRAZOLES, COMPOSITIONS CONTAINING THESE, METHOD OF PRODUCTION AND USE

(75) Inventors: Kirsten Bjergarde, Tuscon, AZ (US); Mark Dodson, Oro Valley, AZ (US); Jacques Mauger, Tuscon, AZ (US); Anil Nair, Tuscon, AZ (US); Marcel Patek, Tuscon, AZ (US); Michel Tabart, La Norville (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 13/156,915

(22) Filed: Jun. 9, 2011

(65) Prior Publication Data
US 2011/0237641 A1   Sep. 29, 2011

Related U.S. Application Data

(60) Division of application No. 12/437,618, filed on May 8, 2009, now Pat. No. 7,989,439, which is a continuation of application No. PCT/FR2007/001851, filed on Nov. 9, 2007.

(30) Foreign Application Priority Data

Nov. 10, 2006   (FR) ...................... 06 09812

(51) Int. Cl.
*C07D 231/10*   (2006.01)
*C07D 231/12*   (2006.01)
(52) U.S. Cl. .................... 548/373.1; 514/407; 435/184; 548/371.7
(58) Field of Classification Search .................. 514/407; 435/184; 548/371.7
See application file for complete search history.

(56) References Cited

U.S. PATENT DOCUMENTS
2004/0220186 A1   11/2004   Bell et al.

FOREIGN PATENT DOCUMENTS

| EP | 1683796 A1 | 7/2006 |
|---|---|---|
| WO | 02088090 A2 | 11/2002 |
| WO | 2004094410 A1 | 11/2004 |
| WO | 2005012256 A1 | 2/2005 |
| WO | 2006003440 A1 | 1/2006 |
| WO | 2006018662 A2 | 2/2006 |
| WO | 2006070198 A1 | 7/2006 |
| WO | 2006077414 A1 | 7/2006 |
| WO | 2006077425 A1 | 7/2006 |
| WO | 2011001122 A2 | 1/2011 |

OTHER PUBLICATIONS

Targat et al. "Synthetic inhibitors of interleukin-6 II: 3,5-diaryl pyridines and meta-terphenyls", Biorganic & Medicinal Chemistry Letters, vol. 5, No. 18, pp. 2143-2146, 1995.
Schafer et al. Drug Discovery Today 2008, 13 (21/22), 913-916.
Horig et al. Journal of Translational Medicine 2004, 2(44).
Sawyer et al. "Synthesis and activity of New Aryl- and heteroaryl-substituted pyrazole inhibitors of the transforming growth factor-β type I receptor kinase domain". Journal of Medicinal Chemistry, vol. 46, No. 19, Sep. 11, 2003.
Wolff Burger's Medicinal Chemistry and Drug Discovery, Fifth Edition, vol. 1: Principles and Practive, Wiley-Interscience 1995, pp. 974-977.
Asahara et al, Tie2 Receptor Ligands, Angiopoietin-1 and Angiopoietin-2, Modulate VEGF-Induced Postnatal Neovascularization, Circ. Res., 1998 (83) pp. 233-240.
Campochiaro, Ocular neovascularisation and excessive vascular permeability, Expert Opin. Biol. Ther., 2004 (4) 9 pp. 1395-1402.
Davis et al, Isolation of Angiopoietin-1, a Ligand for the TIE2 Receptor, by Secretion-Trap Expression Cloning, Cell, 1996 (87) pp. 1161-1169.
Debusk et al, AKT is a major angiogenic mediator downstream of the Ang1/Tie2 signaling pathway, Experimental Cell Research, 2004 (298) pp. 167-177.
Debusk et al, Tie2 Receptor Tyrosine Kinase, a Major Mediator of Tumor Necrosis Factor alpha-Induced Angiogenesis in Rheumatoid Arthritis, Arthritis & Rheumatism, 2003 (48) 9 pp. 2461-2471.
Dumont et al, Dominant-negative and targeted null mutations in the endothelial receptor tyrosine kinase, tek, reveal a critical role in vasculogenesis of the embryo, Genes Dev., 1994 (8) pp. 1897-1909.
Ferrara, Vascular Endothelial Growth Factor and the Regulation of Angiogenesis, Rec. Prog. Horm. Res. 2000 (55) pp. 15-36.
Flokman et al, Angiogenesis in cancer, vascular, rheumatoid and other disease, Nature Med., 1995 (1) 1 pp. 27-31.
Giuliani et al, Proangiogenic properties of human myeloma cells: production of angiopoietin-1 and its potential relationship to myeloma-induced angiogenesis, Blook, 2003 (102) 2 pp. 638-645.
Hangai et al, Systemically Expressed Soluble Tie2 Inhibits Intraocular Neovascularization, Human Gene Therapy, 2001 (12) pp. 1311-1321.
Hasan et al, Intra-tumoural microvessel density in human solid tumors, Br. J. Cancer, 2002 (86) pp. 1566-2577.
Koutroubakis et al, Role of Angiogenesis in Inflammatory Bowel Disease, Inflamm. Bowel Dis., 2006 (12) 6 pp. 515-523.

(Continued)

*Primary Examiner* — Brandon Fetterolf
*Assistant Examiner* — Jean Cornet
(74) *Attorney, Agent, or Firm* — Scully, Scott, Murphy & Presser, P.C.

(57) ABSTRACT

The disclosure relates to a compound of formula (I):

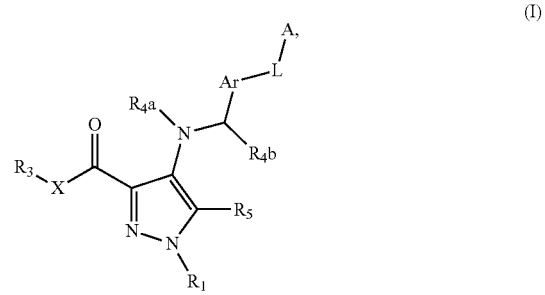

and salts thereof; wherein Ar, L, A, X, $R_1$, $R_2$, $R_3$, $R_4a$, $R_4b$, and $R_5$ are as defined in the disclosure; compositions comprising said compounds, methods for their preparation, intermediates thereto, and the use thereof, particularly as drugs.

23 Claims, No Drawings

OTHER PUBLICATIONS

Kvasnicka et al, Bone marrow angiogenesis: methods of quantification and changes evolving in chronic myeloproliferative disorders, Histol. Histopath., 2004 (19) pp. 1245-1260.

Lee et al, Anti-Vascular Endothelial Growth Factor Treatment Augments Tumor Radiation Response under Normoxic or Hypoxic Conditions 1, Cancer Research, 2000 (60) 19, pp. 5565-5570.

Lin et al, Antiangiogenic gene therapy targeting the endothelium-specific receptor tyrosine kinase Tie2, PNAS, 1998 (95) pp. 8829-8834.

Lin et al, Inhibition of Tumor Angiogenesis Using a Soluble Receptor Establishes a Role for Tie2 in Pathologic Vascular Growth, J. Clin, Invest., 1997 (100) 8 pp. 2072-2078.

Maisonpierre et al, Angiopoietin-2, a Natural Antagonist for Tie2 That Disrupts in vivo Angiogenesis, Science, 1997 (277) pp. 55-60.

Maliba et al, Angiopoietins-1 and -2 are both capable of mediating endothelial PAF synthesis: Intracellular signalling pathways, Cellular Signalling, 2006 (18) pp. 1947-1957.

Melani et al, Angiopoietin decoy secreted at tumor site impairs tumor growth and metastases by inducing local inflammation and altering neoangiogenesis, Cancer Immunol, Immunother., 2004 (53) pp. 600-608.

Millauer et al, Dominant-Negative Inhibition of Flk-1 Suppresses the Growth of Many Tumors Types in Vivo, Cancer Research, 1996 (56) pp. 1615-1620.

Morisada et al, Angiopoietin-1 promotes LYVE-1-positive lymphatic vessel formation, Blood, 2005 (105) 12 pp. 4649-4656.

Nillson et al, Studies on Carbanilic Acid Esters of Cyclic Amino Alcohols. 4. Esters of Pyrrolidinols and Piperidinols as Local Anesthetics, J. Med. Chem., 1971 (14) 8 pp. 710-714.

Pap et al, Linking Angiogenesis to Bone Destruction in Arthritis & Rheumatism, 2005 (52) 5 pp. 1346-1348.

Peters et al, Functional Significance of Tie2 Signaling in the Adult Vasculature, Recent Prog. Horm. Res., 2004 pp. 51-71.

Shahrara et al, Differential expression of the angiogenic Tie receptor family in arthritic and normal synovial tissue, Arthritis Research, 2002 (4) pp. 201-208.

Strawn et al, Flk-1 as a Target for Tumor Growth Inhibition, Cancer Research, 1996 (56) pp. 3540-3545.

Streit et al, Antigiogenesis, Lymphangiogenesis, and Melanoma Metastasis, Oncogene, 2003 (22) pp. 3172-3179.

Suri et al, Requisite Role of Angiopoietin-1, a Ligand for the TIE2 Receptor, during Embryonic Angiogenesis, Cell, 1996 (87) pp. 1171-1180.

Thomas et al, Antiangiogenic Therapy in Lukemia, Acta Haematol., 2001 (106) pp. 190-207.

Xiao et al, Anti-angiogenesis effects of meisoindigo on chronic myelogenous lukemia in vitro, Lukemia Research, 2006 (30) pp. 54-59.

Unites States Office Action dated May 9, 2012 issued in U.S. Appl. No. 13/156,947.

United States Patent Application for U.S. Appl. No. 13/156,947, filed Jun. 9, 2011.

Office Action issued in U.S. Appl. No. 13/156,947 dated Oct. 30, 2012.

SUBSTITUTED PYRAZOLES, COMPOSITIONS CONTAINING THESE, METHOD OF PRODUCTION AND USE

This application is a divisional of U.S. Ser. No. 12/437,618 filed on May 8, 2009, which is a continuation of International Application No. PCT/FR2007/001851, filed Nov. 9, 2007, which is incorporated herein by reference in its entirety; which claims the benefit of priority of French Patent Application No. 0609812, filed Nov. 10, 2006.

The present invention relates especially to novel chemical compounds, particularly substituted pyrazoles, to compositions containing them, and to their use as medicaments.

More particularly, and according to a first aspect, the invention relates to novel specific substituted pyrazoles with anticancer activity, via modulation of the activity of proteins, in particular kinases.

Protein kinases are a family of enzymes that catalyse the phosphorylation of hydroxyl groups of specific residues of proteins such as tyrosine, serine or threonine residues. Such phosphorylations can largely modify the function of proteins; thus, protein kinases play an important role in regulating a wide variety of cell processes, especially including metabolism, cell proliferation, cell differentiation, cell migration or cell survival. Among the various cellular functions in which the activity of a protein kinase is involved, certain processes represent attractive targets for treating cancer diseases and also other diseases.

Thus, one of the objects of the present invention is to propose compositions with anticancer activity, by acting in particular with respect to kinases. Among the kinases for which a modulation of activity is desired, mention may be made of KDR, Tie2, VEGFR-1, PDGFR, FGFR and FLT1. The kinases KDR and/or Tie2 are preferred.

These products correspond to the general formula (I) below:

Formula (I)

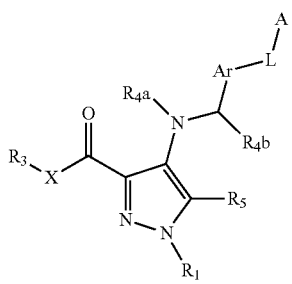

(I)

in which:
1) A and Ar are independently selected from the group consisting of: aryl, heteroaryl, substituted aryl, substituted heteroaryl;
2) L is selected from the group consisting of: NH—CO—NH and O—CO—NH;
3) $R_1$ is selected from the group consisting of: H, $R_6$, $COR_6$, $SO_2R_6$, in which $R_6$ is chosen from H, $OR_7$, $NR_8R_9$, alkyl, cycloalkyl, heterocyclyl, substituted heterocyclyl, aryl, substituted aryl, heteroaryl and substituted heteroaryl, in which $R_7$ is chosen from H, phenyl and alkyl, and in which $R_8$ and $R_9$ are independently selected from the group consisting of H, alkyl, cycloalkyl, heterocyclyl, substituted heterocyclyl, aryl, substituted aryl, heteroaryl and substituted heteroaryl, or alternatively $R_8$ and $R_9$ are linked together to form a saturated 5- to 8-membered ring containing from 0 to 3 heteroatoms chosen from O, S and N;
4) X is selected from the group consisting of: O and NH;
5) $R_3$ is selected from the group consisting of: H, alkyl, substituted alkyl, cycloalkyl, substituted cycloalkyl;
6) $R_{4a}$ is selected from the group consisting of: H and (C1-C4)alkyl;
7) $R_{4b}$ is selected from the group consisting of: H and (C1-C4)alkyl;
8) $R_5$ is selected from the group consisting of: H, halogen, $R_{10}$, CN, $O(R_{10})$, $OC(O)(R_{10})$, $OC(O)N(R_{10})(R_{11})$, $OS(O_2)(R_{10})$, $N(R_{10})(R_{11})$, $N=C(R_{10})(R_{11})$, $N(R_{10})C(O)(R_{11})$, $N(R_{10})C(O)O(R_{11})$, $N(R_{12})C(O)N(R_{10})(R_{11})$, $N(R_{12})C(S)N(R_{10})(R_{11})$, $N(R_{10})S(O_2)(R_{11})$, $C(O)(R_{10})$, $C(O)O(R_{10})$, $C(O)N(R_{10})(R_{11})$, $C(=N(R_{11}))(R_{10})$, $C(=N(OR_{11}))(R_{10})$, $S(R_{10})$, $S(O)(R_{10})$, $S(O_2)(R_{10})$, $S(O_2)O(R_{10})$, $S(O_2)N(R_{10})(R_{11})$; in which each $R_{10}$, $R_{11}$, $R_{12}$ is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl, substituted heterocyclyl.

When $R_1$ is H, the two tautomeric forms indicated below form part of the invention:

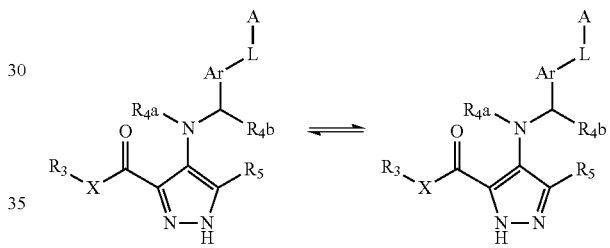

In the products of formula (I), $R_1$ is advantageously H.
In the products of formula (I), $R_3$ is advantageously H and X is advantageously NH, or alternatively $R_3$ is advantageously methyl and X is advantageously O.
In the products of formula (I), $R_5$ is advantageously H.
A substituent Ar according to the invention may be chosen from phenyl, pyridyl, thienyl, furyl and pyrrolyl, substituted with R'$_5$, in which R'$_5$ has the same definition as $R_5$.
In the products of formula (I), Ar-L-A is advantageously:

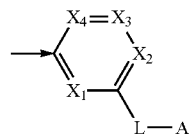

in which each $X_1$, $X_2$, $X_3$ and $X_4$ is independently chosen from N and C—R'$_5$, in which R'$_5$ has the same definition as $R_5$.

More particularly, R'$_5$ may be selected from the group consisting of H, F, Cl, methyl, $NH_2$, $OCF_3$ and $CONH_2$. A substituent Ar is advantageously a phenyl in which R'$_5$ is H.

A substituent A according to the invention may be selected from the group consisting of phenyl, pyridyl, pyrimidyl, thienyl, furyl, pyrrolyl, oxazolyl, thiazolyl, isoxazolyl, isothiazolyl, pyrazolyl, imidazolyl, indolyl, indazolyl, benzimidazolyl, benzoxazolyl and benzothiazolyl; optionally substituted.

More particularly, a substituent A according to the invention may be selected from the group consisting of phenyl, pyrazolyl and isoxazolyl; optionally substituted. A substituent A is advantageously optionally substituted phenyl.

Among the products of formula (I) that are subjects of the present invention, mention may be made especially of a first group of products for which $R_{4a}$ and $R_{4b}$ are H, and A, Ar, L, $R_1$, X, $R_3$ and $R_5$ are as defined above.

Among the products of the first group, mention may be made especially of a first subgroup of products for which:
1) A and Ar are optionally substituted phenyls;
2) L is selected from the group consisting of: NH—CO—NH and O—CO—NH;
3) X is NH and $R_3$ is H, or alternatively X is O and $R_3$ is methyl;
4) $R_1$, $R_{4a}$, $R_{4b}$ and $R_5$ are H.

Among this first subgroup, mention may also be made of a subgroup of products for which:
1) A and Ar are optionally substituted phenyls;
2) L is NH—CO—NH;
3) X is NH and $R_3$ is H;
4) $R_1$, $R_{4a}$, $R_{4b}$ and $R_5$ are H.

Among the products of the first subgroup, mention may be made especially of a second subgroup of products for which:
1) A is an optionally substituted phenyl and Ar is an optionally substituted pyridine;
2) L is selected from the group consisting of: NH—CO—NH and O—CO—NH;
3) X is NH and $R_3$ is H, or alternatively X is O and $R_3$ is methyl;
4) $R_1$, $R_{4a}$, $R_{4b}$ and $R_5$ are H.

Among this second subgroup, mention may be made especially of a subgroup of products for which:
1) A is an optionally substituted phenyl and Ar is an optionally substituted pyridine;
2) L is NH—CO—NH;
3) X is NH and $R_3$ is H.
4) $R_1$, $R_{4a}$, $R_{4b}$ and $R_5$ are H.

Among the products of formula (I) that are subjects of the present invention, mention may be made especially of a second group of products for which $R_{4a}$ is H, $R_{4b}$ is (C1-C4)alkyl, and A, Ar, L, $R_1$, X, $R_3$ and $R_5$ are as defined above.

Among the products of the second group, mention may be made especially of a first subgroup of products for which:
1) A and Ar are optionally substituted phenyls;
2) L is NH—CO—NH;
3) X is NH and $R_3$ is H;
4) $R_1$, $R_{4a}$ and $R_5$ are H;
5) $R_{4b}$ is methyl.

Among the products of formula (I) that are subjects of the present invention, mention may be made especially of a third group of products for which $R_{4a}$ is (C1-C4)alkyl, $R_{4b}$ is H, and A, Ar, L, $R_1$, X, $R_3$ and $R_5$ are as defined above.

Among the products of the third group, mention may be made especially of a first subgroup of products for which:
1) A and Ar are optionally substituted phenyls;
2) L is NH—CO—NH;
3) X is NH and $R_3$ is H;
4) $R_1$, $R_{4b}$ and $R_5$ are H;
5) $R_{4a}$ is methyl.

Among the products of the third group, mention may be made especially of a second subgroup of products for which:
1) A and Ar are optionally substituted phenyls;
2) L is NH—CO—NH;
3) X is NH and $R_3$ is H;
4) $R_1$, $R_{4b}$ and $R_5$ are H;
5) $R_{4a}$ is ethyl.

A may be substituted with one or more substituents selected from the group consisting of: H, F, Cl, Br, I, OH, SH, $SO_3M$, COOM, COO-alkyl, $CON(R_{14})(R_{15})$, CN, $NO_2$, $N(R_{14})CO(R_{15})$, $N(R_{14})(R_{15})$, alkyl, haloalkyl, alkyl-OH, alkyl-$N(R_{14})(R_{15})$, alkyl($R_{16}$), alkyl-COOM, alkyl-$SO_3M$, cycloalkyl, alkylene, alkynyl, aryl, heteroaryl, O-alkyl, O-aryl, O-heteroaryl, S-alkyl, S-aryl and S-heteroaryl, each being optionally substituted with a substituent chosen from alkyl, halogen, O-alkyl and $N(R_{14})(R_{15})$; in which $R_{14}$ and $R_{15}$ are independently chosen from H, alkyl, alkyl-OH, haloalkyl, alkyl-$NH_2$, alkyl-COOM and alkyl-$SO_3M$; in which, when $R_{14}$ and $R_{15}$ are simultaneously other than H, may be bonded to form a 5- to 7-membered ring comprising from 0 to 3 heteroatoms chosen from O, N and S; in which M is H or a cation of an alkali metal chosen from Li, Na and K; and in which $R_{16}$ is H or an optionally substituted non-aromatic heterocycle, containing from 2 to 7 carbon atoms, and 1 to 3 heteroatoms chosen from N, O and S. When A is disubstituted, the two substituents may be linked together to form a 5- to 7-membered ring containing from 0 to 3 heteroatoms chosen from N, O and S.

A may also be substituted with one or more substituents selected from the group mentioned above, also including $SiMe_3$, S—$CHF_3$ and $SF_5$.

More particularly, A may be chosen from phenyl, pyrazolyl or isoxazolyl, substituted with at least one group chosen from H, halogen, alkyl, haloalkyl, O-alkyl, COO-alkyl and O-haloalkyl. A substituent A is advantageously selected from the group consisting of: phenyl, 2-fluoro-5-(trifluoromethyl)phenyl, 2-fluorophenyl, 2-methoxyphenyl, 2-fluoro-3-(trifluoromethyl)phenyl, 3-methoxyphenyl, 3-fluoro-5-(trifluoromethyl)phenyl, 4-(trifluoromethoxy)phenyl, 3-methoxycarbonylphenyl, 4-(trifluoromethyl)phenyl, 3-(trifluoromethyl)phenyl, 2-(trifluoromethyl)phenyl, 3,5-dimethoxyphenyl, 3-methylphenyl, 4-methoxyphenyl, 4-fluorophenyl, 4-chloro-3-(trifluoromethyl)phenyl, 4-(difluoromethoxy)phenyl, 2-chloro-4-(trifluoromethyl)phenyl, 4-methylphenyl, 2,5-dimethylphenyl, 3,4-dimethylphenyl, 2-methylphenyl, 3-ethylphenyl, 3,5-bis(trifluoromethyl)phenyl, 3-fluorophenyl, 2-methoxy-5-methylphenyl, 2,5-dimethoxyphenyl, 3-chloro-4-(difluoromethoxy)phenyl, 2,5-difluorophenyl and 4-methyl-3-(trifluoromethyl)phenyl.

A substituent A is more advantageously selected from the group consisting of: 2-chloro-5-trifluoromethylphenyl, 3-chloro-4-fluorophenyl, 3,4-dichlorophenyl, 3-chloro-5-trifluoromethylphenyl, 3-trimethylsilyl-4-fluorophenyl, 3-trifluoromethoxyphenyl, 4-trifluoromethylpyrid-2-yl, 4-methoxypyrid-2-yl, 3-trifluoromethyl-4-chlorophenyl, 2-chloro-5-trifluoromethylphenyl, 3-trifluoromethylsulfanylphenyl, 3-isopropylphenyl, 3-isopropyl-4-fluorophenyl, 3-pentafluorosulfanylphenyl, 2-methoxy-5-tert-butylphenyl, 4-isopropylphenyl, 2-chloro-4-isopropylphenyl, 2-fluoro-5-methylphenyl, 2-fluoro-4-trifluoromethylphenyl, 2-fluoro-4-methylphenyl, 2-chloro-4-methylphenyl and 2-chloro-5-methylphenyl.

The present invention also comprises the subjects corresponding to combinations of the subgroups mentioned above.

The products according to the invention may be:
1) in non-chiral form, or
2) in racemic form, or
3) enriched in one stereoisomer, or
4) enriched in one enantiomer;
and may optionally be salified.

The present invention also relates to pharmaceutical compositions comprising a product according to the invention in combination with a pharmaceutically acceptable excipient according to the chosen mode of administration. The pharmaceutical composition may be in solid or liquid form or in the form of liposomes.

Among the solid compositions that may be mentioned are powders, gel capsules and tablets. Among the oral forms that may also be included are solid forms protected with respect to the acidic medium of the stomach. The supports used for the solid forms consist especially of mineral supports, for instance phosphates or carbonates, or organic supports, for instance lactose, celluloses, starch or polymers. The liquid forms consist of solutions, suspensions or dispersions. They contain as dispersive support either water or an organic solvent (ethanol, NMP or the like) or mixtures of surfactants and of solvents, or of complexing agents and of solvents.

The liquid forms will preferably be injectable and, as a result, will have a formulation that is acceptable for such a use.

Routes of administration that are acceptable by injection include intravenous, intraperitoneal, intramuscular and subcutaneous routes, the intravenous route usually being preferred.

The administered dose of the compounds of the invention will be adapted by the practitioner as a function of the route of administration to the patient and of the patient's condition.

The products of the invention are useful as inhibitors of a reaction catalysed by a kinase. KDR and/or Tie2 are kinases for which the products of the invention will be particularly useful as inhibitors.

The reasons for which these kinases are chosen are given below:

KDR

KDR (Kinase insert Domain Receptor), also known as VEGF-R2 (Vascular Endothelial Growth Factor Receptor 2), is expressed solely in endothelial cells. This receptor binds to the angiogenic growth factor VEGF, and thus serves as a transduction signal mediator via the activation of its intracellular kinase domain. The direct inhibition of the kinase activity of VEGF-R2 makes it possible to reduce the phenomenon of angiogenesis in the presence of exogenous VEGF (Vascular Endothelial Growth Factor) (Strawn et al., Cancer Research, 1996, vol. 56, p. 3540-3545). This process has especially been demonstrated using VEGF-R2 mutants (Millauer et al., Cancer Research, 1996, vol. 56, p. 1615-1620). The VEGF-R2 receptor appears to have no other function in adults than that associated with the angiogenic activity of VEGF. In addition to this central role in the dynamic angiogenic process, recent results suggest that the expression of VEGF contributes towards the survival of tumoral cells after chemotherapy and radiotherapy, underlining the potential synergy of KDR inhibitors with other agents (Lee et al. Cancer Research, 2000, vol. 60, p. 5565-5570).

Tie2

Tie-2 (TEK) is a member of a family of tyrosine kinase receptors, which is specific to endothelial cells. Tie2 is the first receptor with tyrosine kinase activity for which both the agonist (angiopoietin 1 or Ang1), which stimulates the autophosphorylation of the receptor and cell signalling [S. Davis et al. (1996) Cell 87, 1161-1169], and the antagonist (angiopoietin 2 or Ang2) [P. C. Maisonpierre et al. (1997) Science 277, 55-60] are known. Angiopoietin 1 can synergize with VEGF in the final stages of neoangiogenesis [Asahara T. Circ. Res. (1998) 233-240]. Knock-out experiments and transgenic manipulations of the expression of Tie2 or of Ang1 lead to animals that present vascularization defects [D. J. Dumont et al. (1994) Genes Dev. 8, 1897-1909 and C. Suri (1996) Cell 87, 1171-1180]. The binding of Ang1 to its receptor leads to autophosphorylation of the kinase domain of Tie2, which is essential for neovascularization and also for the recruitment and interaction of blood vessels with the pericytes and smooth muscle cells; these phenomena contribute towards the maturation and stability of the newly formed blood vessels [P. C. Maisonpierre et al. (1997) Science 277, 55-60]. Lin et al. (1997) J. Clin. Invest. 100, 8: 2072-2078 and Lin P. (1998) PNAS 95, 8829-8834 have shown an inhibition of tumour growth and vascularization, and also a reduction in lung metastases, during adenoviral infections or injections of the extracellular domain of Tie-2 (Tek) into models of melanoma and breast tumour xenografts.

For the reasons that follow, the Tie2 inhibitors may be used in situations in which neovascularization or angiogenesis takes place inappropriately, i.e. in cancers in general, but also in particular cancers such as Kaposi's sarcoma or infantile haemoangioma, rheumatoid arthritis, osteoarthritis and/or the associated pain, inflammatory diseases of the intestine such as haemorrhagic rectocolitis or Crohn's disease, eye pathologies such as age-related macular degeneration, diabetic retinopathies, chronic inflammation and psoriasis.

Angiogenesis is a process of generation of new blood capillaries from pre-existing blood vessels. Tumoral angiogenesis (formation of new blood vessels), which is essential for tumoral growth, is also one of the essential factors of metastasic dissemination (Oncogene. 2003 May 19; 22(20):3172-9; Nat. Med. 1995 January; 1(1):27-31).

This neovascularization is due to the migration and then the proliferation and differentiation of endothelial cells under the influence of angiogenic factors secreted by cancer cells and stromal cells (Recent Prog. Horm. Res. 2000; 55:15-35; 35-6).

The angiopoietin 1/Tie2 receptor system plays a predominant role in the maturation of blood vessels by allowing the recruitment of periendothelial cells to stabilize the vessel (Cell. 1996 Dec. 27; 87(7): 1161-9, Recent Prog. Horm. Res. 2004; 59:51-71). Thus, it has been shown that the administration of the soluble recombinant form of the extracellular domain of the Tie2 receptor (exTek) inhibits tumoral angiogenesis in models of murine tumours, and also metastasic growth (Proc. Natl. Acad. Sci. USA. 1998 Jul. 21; 95(15): 8829-34; Cancer Immunol. Immunother. 2004 July; 53(7): 600-8). In endothelial cells in culture, stimulation of Tie2 activates the PI3 kinase route, of p42/p44 routes involved in cell proliferation and migration; of the synthesis of PAF (Cell Signal. 2006 Apr. 14; ahead of print), a route involved in pro-inflammatory activity. Stimulation of Tie2 stimulates the Akt route and inhibits apoptosis (Exp. Cell Res. 2004 Aug. 1; 298(1): 167-77), a transduction route known for its importance in cell survival.

The addition of exTek (soluble receptor of Tie2) inhibits the formation of pseudotubules of endothelial cells on Matrigel (Cancer Immunol. Immunother. 2004 July; 53(7): 600-8). These studies indicate that the Tie2/angiopoietin system is necessary during the first stages of formation of vascular buds in adult tissues and that one function of the Tie2 receptor is to increase the survival of endothelial cells during the formation of blood vessels. Furthermore, angiopoietin-1 stimulates the proliferation of lymphatic endothelial cells and also lymphangiogenesis (development of new lymphatic vessels), a favored route of access for metastasic growth (Blood. 2005 Jun. 15; 105(12): 4649-56).

Angiogenesis processes also play a predominant role in the progression of numerous solid tumours. Furthermore, it has been shown that the probability of onset of metastases increases very greatly as the vascularization of the primary tumour increases (Br. J. Cancer. 2002 May 20; 86(10): 1566-77).

The potential role of pro-angiogenic agents in leukaemias and lymphomas has also more recently been documented. Specifically, it has been reported in general that cell clones in these pathologies may be either naturally destroyed by the immune system, or revert to an angiogenic phenotype that favors their survival and then their proliferation. This change in phenotype is induced by an overexpression of angiogenic factors especially by the macrophages and/or mobilization of these factors from the extracellular matrix (Thomas D A, Giles F J, Cortes J, Albitar M, Kantarjian H M., Acta Haematol., (2001), vol 207, pp. 106-190).

There is a correlation between the angiogenesis process of bone marrow and "extramedullar diseases" in CML (chronic myelomonocytic leukaemia). Various studies demonstrate that the inhibition of angiogenesis might represent a treatment of choice in this pathology (Leuk. Res. 2006 January; 30(1): 54-9; Histol. Histopathol. 2004 October; 19(4): 1245-60). Furthermore, it is strongly suggested that activation of the Tie2/angiopoietin system is involved in the development of angiogenesis of bone marrow in the case of patients suffering from multiple myeloma (Blood. 2003 Jul. 15; 102(2): 638-45).

Rheumatoid arthritis (RA) is a chronic disease whose etiology is unknown. Although it affects many organs, the most severe form of RA is progressive synovial inflammation of the joints resulting in their destruction. Angiogenesis appears to substantially affect progression of this pathology. Thus, it has been shown that activation of Tie2 regulates angiogenesis in synovial tissues, promoting the development of rheumatoid arthritis (Arthritis Rheum. 2003 September; 48(9): 2461-71).

It has also been shown that an overexpression of angiopoietin-1 and of Tie2 in the synovial tissues of patients suffering from osteoarthritis is correlated to active neovascularization (Shahrara S et al., Arthritis Res. 2002; 4(3)). Thus, it has been shown that by blocking the activation of Tie2 by using an adenovirus that produces exTek (soluble Tie2 receptor), an inhibition of angiogenesis, of the development of arthrosis and protection against bone degradation are obtained in a mouse model in which the arthrosis is induced with collagen (Arthritis Rheum. 2005 May; 52(5):1346-8).

IBDs (inflammatory bowel disease) comprise two forms of chronic inflammatory diseases of the intestine: UC (ulcerative colitis) and Crohn's disease (CD). IBDs are characterized by an immune dysfunction that is reflected by an inappropriate production of inflammatory cytokines, inducing the establishment of a local microvascular system. This angiogenesis of inflammatory origin results in a vasoconstriction-induced intestinal ischaemia (Inflamm. Bowel Dis. 2006 June; 12(6):515-23).

Eye pathologies in relation with neovascularization phenomena, such as age-related macular degeneration, are responsible for a large majority of the cases of blindness in developed countries. The molecular signals that control the neovascularization phenomena in the eye, such as VEGFs or angiopoietins, are targets of choice for these pathologies (Campochiaro P A. Expert Opin. Biol. Ther. 2004 September; 4(9)). Thus, it has been shown that blocking the activation of Tie2 by using an adenovirus that produces exTek (soluble Tie2 receptor) inhibits retinol and choroid neovascularization, which is the most common cause of loss of vision (Hum. Gene Ther. 2001 Jul. 1; 12(10):1311-21).

A product in accordance with the invention may be used for the manufacture of a medicament that is useful for treating a pathological condition, in particular a cancer.

By virtue of their low toxicity and their pharmacological and biological properties, the compounds of the present invention find their application in the treatment of any carcinoma having a substantial degree of vascularization or inducing metastases, or, finally, in pathologies of the type such as lymphomas and leukaemias.

These compounds represent a treatment of choice either alone or in combination with a suitable chemotherapy or radiotherapy and/or in combination with other compounds having anti-angiogenic activity, for instance VEGF or FGF inhibitors. Thus, the products of general formula (I) are especially useful for treating or preventing a pathological condition, characterized in that the product is administered alone or in combination with other active principles, especially anti-cancer agents such as cytotoxic, cytostatic, anti-angiogenic or anti-metastasic products.

The compounds of the present invention may thus be administered alone or as a mixture with other anticancer agents. Among the possible combinations that may be mentioned are:

alkylating agents and especially cyclophosphamide, melphalan, ifosfamide, chlorambucil, busulfan, thiotepa, prednimustine, carmustine, lomustine, semustine, streptozotocin, decarbazine, temozolomide, procarbazine and hexamethylmelamine;

platinum derivatives such as, especially, cisplatin, carboplatin or oxaliplatin;

antibiotics such as, especially, bleomycin, mitomycin or dactinomycin;

antimicrotubule agents such as, especially, vinblastine, vincristine, vindesine, vinorelbine and taxoids (paclitaxel and docetaxel);

anthracyclines such as, especially, doxorubicin, daunorubicin, idarubicin, epirubicin, mitoxantrone and losoxantrone;

group I and II topoisomerase inhibitors such as etoposide, teniposide, amsacrine, irinotecan, topotecan and tomudex;

fluoropyrimidines such as 5-fluorouracil, UFT and floxuridine;

cytidine analogues such as 5-azacytidine, cytarabine, gemcitabine, 6-mercaptomurine and 6-thioguanine;

adenosine analogues such as pentostatin, cytarabine or fludarabine phosphate methotrexate and folinic acid;

various enzymes and compounds such as L-asparaginase, hydroxyurea, trans-retinoic acid, suramine, dexrazoxane, amifostine and herceptin, and also oestrogen-based and androgenic hormones;

antivascular agents such as combretastatin derivatives, for example CA4P, chalcone or colchicine derivatives, for example ZD6126, and prodrugs thereof;

anti-angiogenic agents such as bevacizumab, sorafenib or sunitinib malate; and therapeutic agents that inhibit other tyrosine kinases, such as imatinib, gefitinib and erlotinib.

When the compounds of the present invention are combined with another treatment or with a radiation treatment, these treatments may then be administered simultaneously, separately or sequentially. The treatment will be adapted by the practitioner as a function of the disease to be treated.

Definitions

The term "halogen" refers to an element chosen from F, Cl, Br and I.

The term "alkyl" refers to a linear or branched saturated hydrocarbon-based substituent containing from 1 to 6 carbon atoms. The substituents methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1- dimethylpropyl, 1,2-dimethylpropyl, 2,2-dimethylpropyl, 1-ethylpropyl, hexyl, 1-methylpentyl, 2-methylpentyl, 1-ethylbutyl, 2-ethylbutyl and 3,3-dimethylbutyl are examples of alkyl substituents.

The term "alkylene" refers to a linear or branched hydrocarbon-based substituent containing one or more unsaturations, and containing from 2 to 6 carbon atoms. The substituents ethylenyl, 1-methylethylenyl, prop-1-enyl, prop-2-enyl, Z-1-methylprop-1-enyl, E-1-methylprop-1-enyl, Z-1,2-dimethylprop-1-enyl, E-1,2-dimethylprop-1-enyl, but-1,3-dienyl, 1-methylidenylprop-2-enyl, Z-2-methylbut-1,3-dienyl, E-2-methylbut-1,3-dienyl and 2-methyl-1-methylidenylprop-2-enyl are examples of alkylene substituents.

The term "alkynyl" refers to a linear or branched hydrocarbon-based substituent containing at least two unsaturations borne by a pair of vicinal carbon atoms, and containing from 2 to 6 carbon atoms. The substituents ethynyl; prop-1-ynyl; prop-2-ynyl; and but-1-ynyl are examples of alkynyl substituents.

The term "aryl" refers to a monocyclic or polycyclic aromatic substituent containing from 6 to 14 carbon atoms. The substituents phenyl, naphth-1-yl; naphth-2-yl; anthracen-9-yl; 1,2,3,4-tetrahydronaphth-5-yl; and 1,2,3,4-tetrahydronaphth-6-yl are examples of aryl substituents.

The term "heteroaryl" refers to a monocyclic or polycyclic heteroaromatic substituent containing from 1 to 13 carbon atoms and from 1 to 4 heteroatoms. The substituents pyrrol-1-yl; pyrrol-2-yl; pyrrol-3-yl; furyl; thienyl; imidazolyl; oxazolyl; thiazolyl; isoxazolyl; isothiazolyl; 1,2,4-triazolyl; oxadiazolyl; thiadiazolyl; tetrazolyl; pyridyl; pyrimidyl; pyrazinyl; 1,3,5-triazinyl; indolyl; benzo[b]furyl; benzo[b]thienyl; indazolyl; benzimidazolyl; azaindolyl; quinolyl; isoquinolyl; carbazolyl; and acridyl are examples of heteroaryl substituents.

The term "heteroatom" refers herein to an at least divalent atom other than carbon. N; O; S; and Se are examples of heteroatoms.

The term "cycloalkyl" refers to a saturated or partially unsaturated cyclic hydrocarbon-based substituent containing from 3 to 12 carbon atoms. The substituents cyclopropyl; cyclobutyl; cyclopentyl; cyclopentenyl; cyclopentadienyl; cyclohexyl; cyclohexenyl; cycloheptyl; bicyclo[2.2.1]heptyl; cyclooctyl; bicyclo[2.2.2]octyl; adamantyl; and perhydronaphthyl are examples of cycloalkyl substituents.

The term "heterocyclyl" refers to a saturated or partially unsaturated cyclic hydrocarbon-based substituent containing from 1 to 13 carbon atoms and from 1 to 4 heteroatoms. Preferably, the saturated or partially unsaturated cyclic hydrocarbon-based substituent will be monocyclic and will contain 4 or 5 carbon atoms and 1 to 3 heteroatoms.

The term "substituted" refers to one or more substituents other than H, for example halogen; alkyl; aryl; heteroaryl; cycloalkyl; heterocyclyl; alkylene; alkynyl; OH; O-alkyl; O-alkylene; O-aryl; O-heteroaryl; $NH_2$; NH-alkyl; NH-aryl; NH-heteroaryl; N-alkyl-alkyl', in which alkyl' and alkyl are two identical or different alkyls; SH; S-alkyl; S-aryl; $S(O_2)H$; $S(O_2)$-alkyl; $S(O_2)$-aryl; $SO_3H$; $SO_3$-alkyl; $SO_3$-aryl; CHO; C(O)-alkyl; C(O)-aryl; C(O)OH; C(O)O-alkyl; C(O)O-aryl; OC(O)-alkyl; OC(O)-aryl; $C(O)NH_2$; C(O)NH-alkyl; C(O)NH-aryl; NHCHO; NHC(O)-alkyl; NHC(O)-aryl; NH-cycloalkyl; and NH-heterocyclyl.

A subject of the present invention is also the process for preparing the products of general formula (I) below:

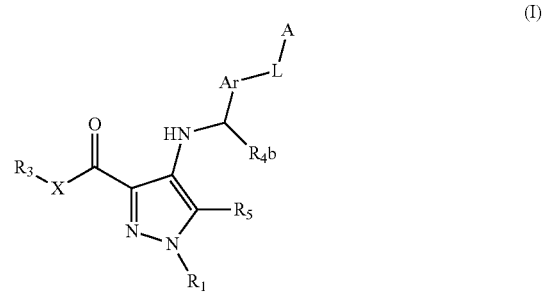

(I)

in which $R_1$, $R_3$, $R_{4b}$, $R_5$, X, Ar, L and A are as defined above, characterized in that a product of general formula (II) below:

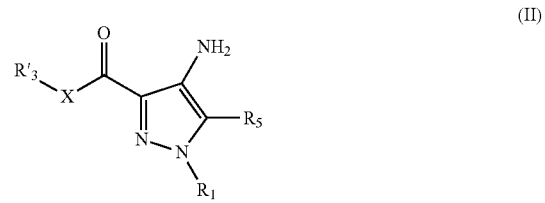

(II)

in which $R'_3$ is $R_3$ or a precursor of $R_3$, and X, $R_1$, $R_3$ and $R_5$ are as defined above, reacts with a product of formula (III) below:

(III)

in which $R_{4b}$, Ar, L and A are as defined above, to give the product of general formula (I).

A subject of the present invention is also, as intermediate products, the products of general formula (II), for which $R'_3$, X, $R_1$ and $R_5$ are as defined above, and also the products of general formula (III), for which Ar, L and A are as defined above.

A subject of the present invention is also the process for preparing the intermediate products of general formula (II) below:

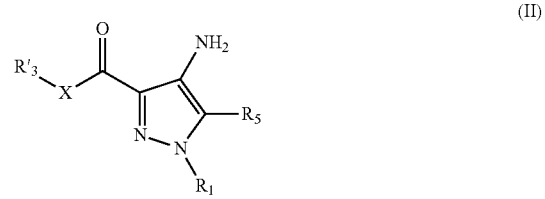

(II)

in which R'$_3$, X, R$_1$ and R$_5$ are as defined above, characterized in that a product of general formula (IV) below:

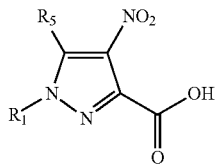
(IV)

in which R$_1$ and R$_5$ are as defined above, reacts with a product of general formula (V) below:

(V)

in which Gp is a protecting group, X and R'$_3$ are as defined above, to give the product of general formula (II).

A subject of the present invention is also the process for preparing the intermediate products of general formula (III) below:

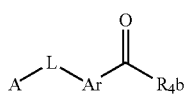
(III)

in which R$_{4b}$, Ar and A are as defined above, and L is NH—CO—NH, characterized in that a product of general formula (VI) below:

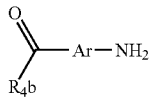
(VI)

in which R$_{4b}$, Ar is as defined above, reacts with a product of general formula (VII) below:

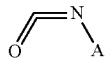
(VII)

in which A is as defined above, to give the product of general formula (III).

A subject of the present invention is also a process for preparing the products of general formula (I)

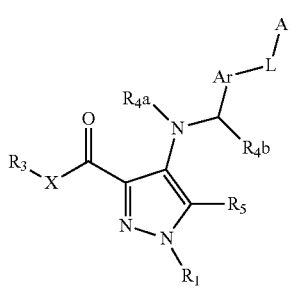
(I)

in which R$_1$, R$_3$, R$_{4a}$, R$_{4b}$, R$_5$, X, Ar and A are as defined above, and L is NHCONH, characterized in that a product of general formula (VIII) below:

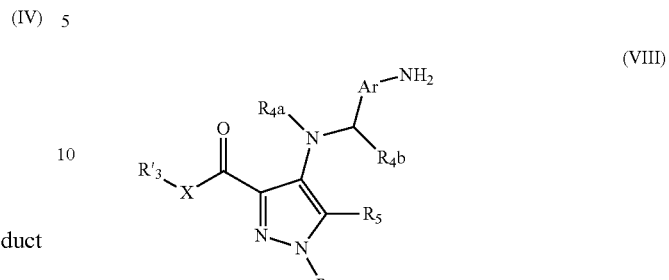
(VIII)

in which R'$_3$ is R$_3$ or a precursor of R$_3$, and X, R$_1$, R$_3$, R$_{4a}$, R$_{4b}$ and R$_5$ are as defined above, reacts with a product of formula (VII) below:

(VII)

in which A is as defined above, to give the product of general formula (I') below

(I')

in which the precursor R'$_3$ is transformed into R$_3$ in order to obtain the product of general formula (I).

A subject of the present invention is also the process for preparing the intermediate products of general formula (VIII)

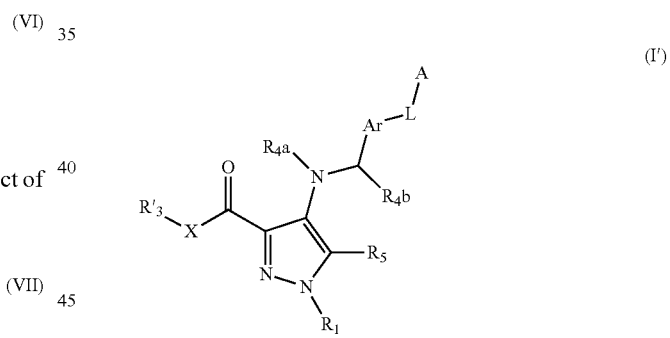
(VIII)

in which R'₃ is R₃ or a precursor of R₃, and Ar, X, R₁, R₃, R₄ₐ, R₄ᵦ and R₅ are as defined above, characterized in that a product of general formula (IX) below:

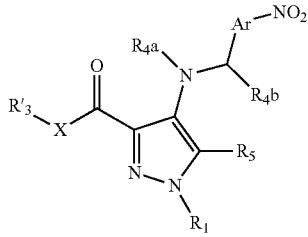
(IX)

undergoes a reduction to give a product of general formula (VIII).

A subject of the present invention is also the process for preparing the intermediate products of general formula (IXa)

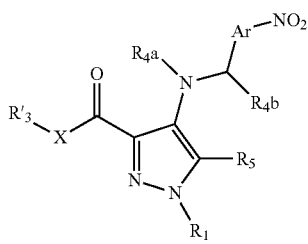
(IXa)

in which R'₃ is R₃ or a precursor of R₃, R₄ₐ is (C1-C4)alkyl, and R₄ᵦ is H, and X, R₁, R₃ and R₅ are as defined above, characterized in that a product of general formula (IXc) below:

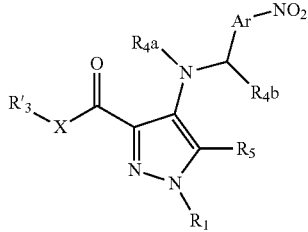
(IXc)

in which R'₃ is R₃ or a precursor of R₃, R₄ₐ and R₄ᵦ are H, and X, R₁, R₃ and R₅ are as defined above, undergoes an aminoalkylation to give a product of general formula (IXa) above.

A subject of the present invention is also the process for preparing the intermediate products of general formula (IXc)

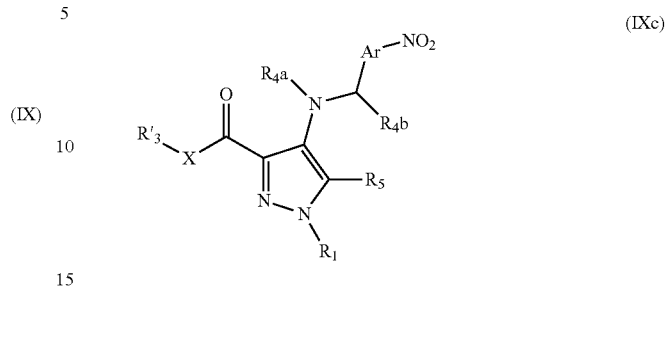
(IXc)

in which R'₃ is R₃ or a precursor of R₃, R₄ₐ and R₄ᵦ are H, and Ar, X, R₁, R₃ and R₅ are as defined above, characterized in that a product of general formula (II) below:

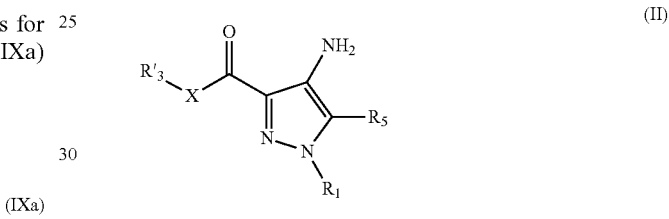
(II)

in which R'₃, X, R₁ and R₅ are as defined above, reacts with a product of general formula (Xc) below:

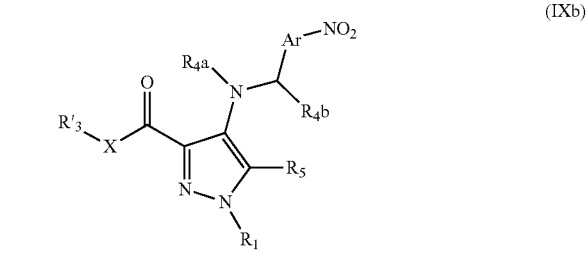
(Xc)

in which R₄ᵦ is H and Ar is as defined above, to give a product of general formula (IXc) above.

A subject of the present invention is also the process for preparing the intermediate products of general formula (IXb)

(IXb)

in which R'$_3$ is R$_3$ or a precursor of R$_3$, R$_{4a}$ is H, and R$_{4b}$ is (C1-C4)alkyl, and Ar, X, R$_1$, R$_3$ and R$_5$ are as defined above, characterized in that a product of general formula (II) below:

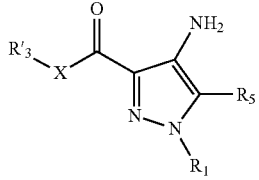
(II)

in which R'$_3$, X, R$_1$ and R$_5$ are as defined above, reacts with a product of general formula (Xb) below:

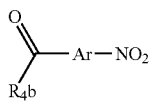
(Xb)

in which R$_{4b}$ is (C1-C4)alkyl and Ar is as defined above, and then undergoes a reduction to give a product of general formula (IXb) above.

The starting materials used are commercially available or are prepared by methods known to those skilled in the art.

The term "protecting group Gp" means a group that makes it possible, on the one hand, to protect reactive functions such as a hydroxyl or an amine during a synthesis, and, on the other hand, to regenerate the intact reactive function at the end of the synthesis.

Examples of protecting groups and of protection and deprotection methods are given in "Protective Groups in Organic Synthesis", Green et al., 2$^{nd}$ Edition (John Wiley & Sons, Inc., New York).

The term "precursor of R$_3$" means a group which makes it possible to generate, at the end of the reaction or synthesis, a group R$_3$. It is, for example, a —CH$_2$-Rink resin when X is NH, or a 2,4-dimethoxybenzyl group.

The product according to the invention may be prepared using conventional methods of organic chemistry. Scheme 1 below illustrates the methods used for the preparation of Examples 1 to 31. In this respect, it shall not constitute a limitation of the scope of the invention, as regards the methods for preparing the claimed compounds.

Scheme 1

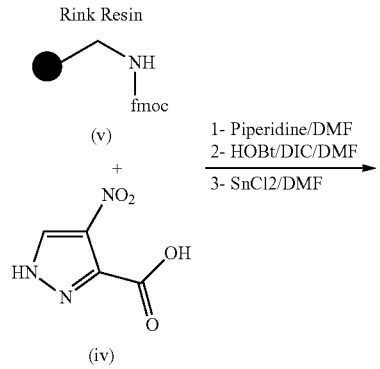

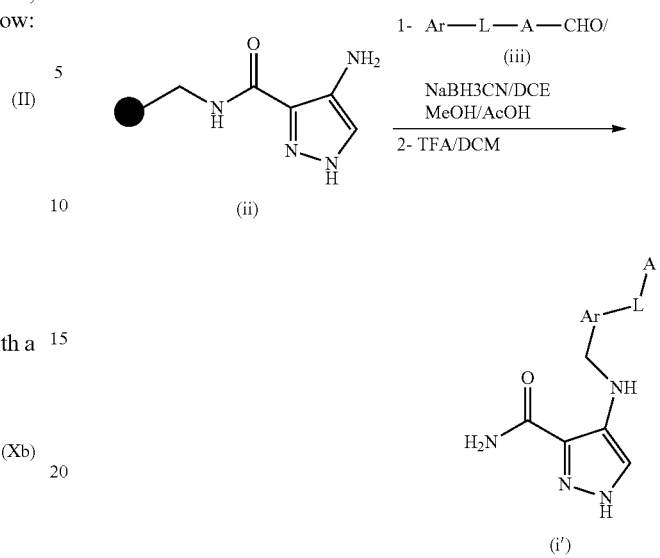

1—Preparation of the Intermediate Resin (ii)

The Rink resin (v) is swollen in DMF. The DMF is filtered off and then replaced with a 50% solution of piperidine in DMF. After stirring for 30 minutes at room temperature, the mixture is filtered and the resin is then successively washed with DMF, methanol and DMF.

Next, a solution of 3 equivalents of 4-nitro-3-pyrazolecarboxylic acid (iv), 3 equivalents of HOBt (hydroxybenzotriazole) and 3 equivalents of diisopropylcarbodiimide (DIC) in DMF is added to the resin. The mixture is stirred overnight at room temperature and the reaction mixture is then removed by filtration. The resin is washed three times with DMF, twice with methanol and five times with DMF. The resin is then treated with molar tin chloride (SnCl$_2$) solution overnight at room temperature. The reaction mixture is removed by filtration. The resin is washed five times with DMF, twice with methanol, three times with DCM (dichloromethane) and twice with ether, and then dried under vacuum to give the resin (ii).

2—Preparation of the Products (i') by Reductive Amination

In a vial, the resin (ii) is swollen in dichloroethane (DCE). 3 equivalents of aldehyde (iii) dissolved in DMF are added, followed by 5 equivalents of sodium cyanoborohydride in methanol containing 10% acetic acid. The mixture is maintained at 80° C. for 2 hours. After cooling, the reaction medium is filtered and the resin is washed successively twice with methanol, three times with DCM (dichloromethane), twice with methanol and three times with DCM. The final products are obtained by cleavage with a trifluoroacetic acid/DCM solution (50/50) at room temperature for two hours. The product is isolated by filtration and evaporation of the solvent. The product (i') is purified either by normal-phase liquid chromatography or by preparative LC/MS.

Materials and Methods

LC/MS Analytical Method A:

The analysis is performed on a Waters ZQ model mass spectrometer in negative and positive electrospray mode (range from 10 to 1200 amu) connected to an Agilent HP 1100 HPLC instrument. The separation is performed on a Waters Xbridge C18 column (3×50 mm, 2.5 μm particle diameter) maintained at 60° C., using an acetonitrile/water gradient containing 0.1% (v/v) of formic acid and at a flow rate of 1.1 ml/minute. The gradient rises from 5% to 100% acetonitrile over 5 minutes, is maintained at 100% for 30 seconds and is then returned to 5% over 1 minute. The total separation time is 7 minutes. In addition to the mass spectroscopy analysis, a UV detection (diode array) is performed at wavelengths of from 210 to 400 nm, along with an ELSD measurement (evaporative light scattering) using a Sedere Sedex 85 instrument.

LC/MS Analytical Method B:

The analysis is performed on a Waters model ZQ mass spectrometer in negative and positive electrospray mode (range from 10 to 1200 amu) connected to a Waters Alliance HT instrument. The separation is performed on a Waters Atlantis dC18 column of (2.1×50 mm, 5 μm particle diameter) maintained at 25° C., using an acetonitrile/water gradient containing 0.1% (v/v) of trifluoroacetic acid and at a flow rate of 0.5 ml/minute. The gradient rises from 5% to 85% acetonitrile over 5 minutes, and is then maintained at 90% for 1 minute. The total separation time is 7 minutes. In addition to the mass spectroscopy analysis, a UV detection (diode array) is performed at wavelengths of from 210 to 400 nm.

LC/MS Method Preparative C:

The products are purified by preparative LC/MS using a Waters FractionLynx system composed of a Waters model 600 pump for the gradient, a Waters model 515 pump for the regeneration, a Waters Reagent Manager pump, a model 2700 auto-injector, two LabPro model Theodyne switches, a Waters diode array detector, a Waters ZMD model mass spectrometer and a model 204 fraction collector. The instrument is run by the Waters FractionLynx software. At the outlet of the separation column, 1/1000 of the flow is diverted by means of an LC Packing Accurate splitter; this flow is mixed with methanol (flow rate 0.5 ml/minute) and sent to the detectors: 3/4 is sent to the diode array and 1/4 to the mass spectrometer; the rest of the flow (999/1000) is sent to the fraction collector. The product is collected if the mass peak is observed by FractionLynx, otherwise the flow is directly discarded. The molecular formulae of the products are transferred to the FractionLynx software and the product is collected when the mass peaks [M+H]+ and [M+Na]+ are detected. The fractions are collected in vials, which are evaporated in a Jouan model RC10.10 rotary evaporator. The weight of product obtained is determined by measuring the weight of the vial after evaporation of the solvent. The information regarding the columns and the gradients used is given for each example in the following section.

LC/MS Analytical Method D:

The analysis is performed on a Waters SQD mass spectrometer in negative and positive electrospray mode (range from 10 to 1200 amu) connected to a Waters Alliance HT instrument. The separation is performed on a BEH column (2.1×50 mm, 1.7 μm particle diameter) maintained at 25° C., using an acetonitrile/water gradient containing 0.1% (v/v) of trifluoroacetic acid and at a flow rate of 1 ml/minute. The gradient rises from 5% to 100% acetonitrile over 2 minutes. In addition to the mass spectroscopy analysis, a UV detection (diode array) is performed at wavelengths of from 210 to 400 nm.

EXAMPLE 1

4-{[3-phenyl]carbamoyl}oxy)benzyl]amino}-1H-pyrazole-3-carboxamide trifluoroacetate

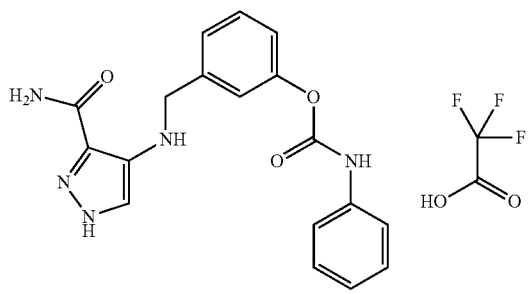

Preparation of the Resin (ii):

30 g of Rink resin (PolymerLab; 0.99 mmol/g) is swollen in 150 ml of DMF. After stirring for 10 minutes, the DMF is filtered off and replaced with 150 ml of a solution of piperidine in DMF (50/50, v/v). The mixture is stirred for 1 hour and then filtered. The resin is washed successively with five times 150 ml of DMF, twice 150 ml of methanol and three times 150 ml of DMF. Next, a solution of 14.1 g of 4-nitro-3-pyrazole-carboxylic acid (90 mmol, 3 eq.) and 13.8 g of HOBt (90 mmol, 3 eq.) in 150 ml of DMF is added to the resin, immediately followed by 13.8 ml of DIC (90 mmol; 3 eq.). The mixture is stirred for 16 hours at room temperature. The solution is filtered and the resin is washed successively with five times 150 ml of DMF, twice 150 ml of methanol, three times 150 ml of DMF and then with 150 ml of a 1M SnCl$_2$ solution (33 g in 150 ml). The mixture is stirred at room temperature for 24 hours and is then filtered, and the resin is washed with five times 150 ml of DMF, twice 150 ml of methanol, three times 150 ml of DCM and twice 150 ml of ethyl ether. After drying under vacuum, 31 g of intermediate resin (ii) are isolated.

Preparation of Example 1:

100 mg of resin (ii) are swollen in 0.3 ml of DCE, and 72 mg of phenylcarbamic acid 3-formylphenyl ester (0.3 mmol; ~3 eq.) dissolved in 0.2 ml of DMF are then added, followed by 33 mg of sodium cyanoborohydride (0.5 mmol; ~5 eq.). The mixture is heated at 80° C. for 1 hour, and then filtered after cooling to room temperature. The resin is then washed successively with twice 1 ml of MeOH, five times 1 ml of DMF, three times 1 ml of MeOH and five times 1 ml of DCM. The product is cleaved by treating the resin with 1 ml of a 50/50 TFA/DCM solution. The solution is evaporated and the crude product obtained is directly purified by preparative HPLC. 2.4 mg of expected product 1 are obtained (yield=5%). ([M+H]+): 352). RT=2.49 min (Method A).

EXAMPLE 2a

4-{[3-({[2-fluoro-5-(trifluoromethyl)phenyl]carbamoyl}amino)benzyl]-amino}-1H-pyrazole-3-carboxamide trifluoroacetate and Example 2b: 4-{[3-({[2-fluoro-5-(trifluoromethyl)phenyl]carbamoyl}amino)benzyl]amino}-1H-pyrazole-3-carboxamide hydrochloride

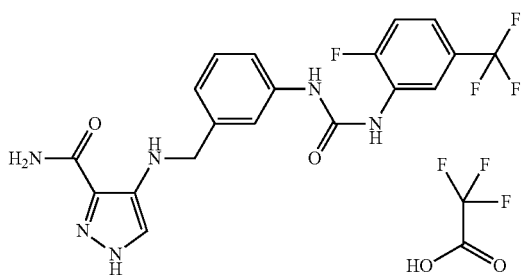

and

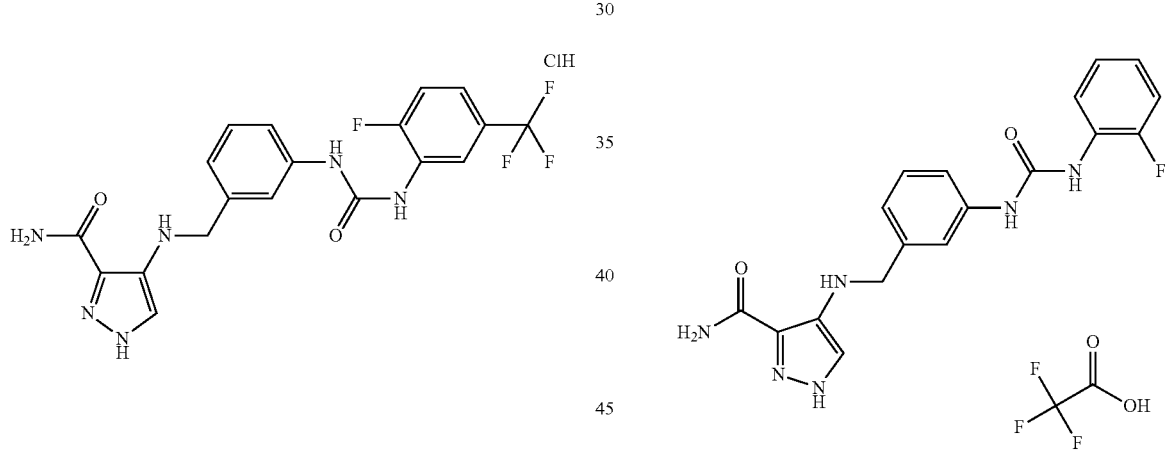

Preparation of 1-(2-fluoro-5-trifluoromethylphenyl)-3-(3-formylphenyl)urea

A mixture of 484 mg of 3-aminobenzaldehyde (4 mmol) (polymerized form) and 290 μl of 2-fluoro-5-trifluoromethylphenyl isocyanate in 4 ml of DCE is treated in a CEM Discover microwave oven at 100° C. for 10 minutes (power 90). After cooling, the mixture is poured into 100 ml of saturated potassium hydrogen sulfate solution and extracted with twice 50 ml of ethyl acetate. The combined organic phases are washed with water, dried over sodium sulfate and evaporated. 740 mg of the expected aldehyde (yield=57%) are obtained in an LC/MS purity of 82%. The crude product is used directly for the following steps. ([M+H]+): 327. RT=4.28 min (acetonitrile/water gradient from 30% to 90%—Method B).

Preparation of Example 2a:

Example 2a was prepared according to the method described for Example 1, starting with 1 g of resin (ii), 520 mg of 1-(2-fluoro-5-trifluoromethylphenyl)-3-(3-formylphenyl)urea (1.6 mmol, 2 eq.) and 264 mg of sodium cyanoborohydride (4 mmol; ~5 eq.). After purification by preparative HPLC, product 2a is obtained (EIMS ([M+H]+): 437. RT=3.45 min. (Method A).

Preparation of Example 2b:

Example 2b was prepared according to the method described for Example 1, starting with 1 g of resin (ii), 520 mg of 1-(2-fluoro-5-trifluoromethylphenyl)-3-(3-formylphenyl)urea (1.6 mmol, 2 eq.) and 264 mg of sodium cyanoborohydride (4 mmol; ~5 eq.). After filtration and evaporation, 301 mg of crude product are isolated (LC/MS purity 83%). The crude product is purified on a column of silica using a DCM/MeOH mixture (90/10) as eluent. 151 mg of pale yellow solid are isolated (43% yield). The product is dissolved in 2 ml of MeOH and is converted into its hydrochloride salt by addition of a 4N solution of HCl in dioxane. After evaporation, the product 2b is isolated in the form of a pale yellow solid. (EIMS ([M+H]+): 437. RT=3.45 min. (Method A). $^1$H NMR ($D_6$-MeOD) (600 MHz): 4.62 (s, 2H); 7.19 (d, 1H); 7.36 (2s, 2H); 7.40 (m, 1H); 7.49 (m, 1H); 7.76 (s, 1H); 7.78 (s, 1H); 8.62 (m, 1H).

EXAMPLE 3

4-[(3-{[(2-fluorophenyl)carbamoyl]amino}benzyl)amino]-1H-pyrazole-3-carboxamide trifluoroacetate

Preparation of 1-(2-fluorophenyl)-3-(3-formylphenyl)urea

The product was prepared as described in Example 2, starting with 484 mg of 3-amino-benzaldehyde (4 mmol) (polymerized form) and 548 mg of 2-fluorophenyl isocyanate in 4 ml of DCE. After cooling, the mixture is poured into 100 ml of saturated potassium hydrogen sulfate solution and extracted with twice 50 ml of ethyl acetate. The combined organic phases are washed with water, dried over sodium sulfate and evaporated. 864 mg of the expected aldehyde are isolated in the form of a gum, in an LC/MS purity of 77%. A crystallized fraction is obtained after trituration from ethyl ether. 165 mg of solid are isolated ([M+H]+): 259. RT=4.28 min (acetonitrile/water gradient from 5% to 85%—Method B).

Preparation of Example 3:

Example 3 was prepared according to the method described for Example 1, starting with 200 mg of resin (ii), 104 mg of 1-(2-fluorophenyl)-3-(3-formylphenyl)urea (0.4 mmol, 2 eq.) and 66 mg of sodium cyanoborohydride (1 mmol; ~5 eq.). After purification by preparative HPLC, 33 mg of product 3 are isolated. (yield=43%). EIMS ([M+H]+): 369. RT=3.70 min (acetonitrile/water gradient from 5% to 85%—Method A).

EXAMPLE 4

4-[(3-{[(2-methoxyphenyl)carbamoyl]amino}benzyl)amino]-1H-pyrazole-3-carboxamide trifluoroacetate

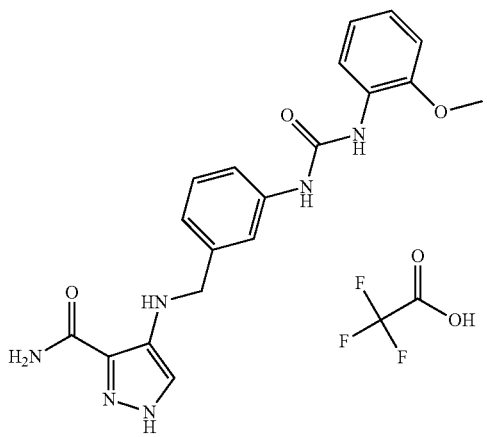 [SMILES: COc1ccccc1NC(=O)Nc1cccc(CNc2c[nH]nc2C(N)=O)c1 ; O=C(O)C(F)(F)F]

Preparation of 1-(2-methoxyphenyl)-3-(3-formylphenyl)urea

The product was prepared as described in Example 2, starting with 484 mg of 3-amino-benzaldehyde (4 mmol) (polymerized form) and 597 mg of 2-methoxyphenyl isocyanate (4 mmol) in 4 ml of DCE. 300 mg of crude expected aldehyde are isolated and used directly in the following step. ([M+H]+): 271. RT=5.14 min (acetonitrile/water gradient from 30% to 90%—Method B).

Preparation of Example 4:

Example 4 was prepared according to the method described for Example 1, starting with 200 mg of resin (ii), 162 mg of 1-(2-methoxyphenyl)-3-(3-formylphenyl)urea (0.6 mmol, 3 eq.) and 66 mg of sodium cyanoborohydride (1 mmol; ~5 eq.). After purification by preparative HPLC, 10.4 mg of product 4 are isolated. (yield=11%). EIMS ([M+H]+): 381. RT=3.84 min (acetonitrile/water gradient from 5% to 85%—Method A).

EXAMPLE 5

4-{[3-({[2-fluoro-3-(trifluoromethyl)phenyl]carbamoyl}amino)benzyl]-amino}-1H-pyrazole-3-carboxamide trifluoroacetate

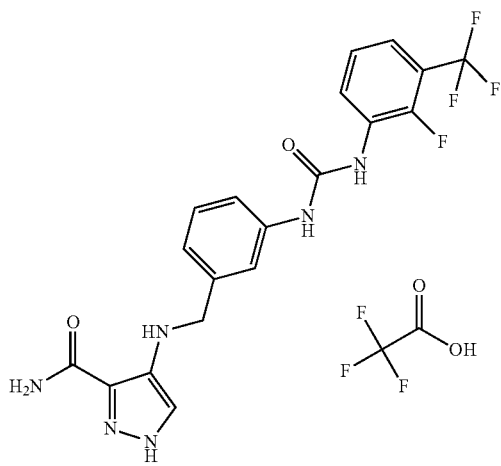 [SMILES: NC(=O)c1n[nH]cc1NCc1cccc(NC(=O)Nc2cccc(C(F)(F)F)c2F)c1 ; O=C(O)C(F)(F)F]

Preparation of 1-(2-fluoro-3-trifluoromethylphenyl)-3-(3-formylphenyl)urea

The product was prepared as described in Example 2, starting with 484 mg of 3-amino-benzaldehyde (4 mmol) (polymerized form) and 820 mg of 2-fluoro-3-trifluoromethylphenyl isocyanate (4 mmol) in 4 ml of DCE. 300 mg of crude expected aldehyde are isolated and used directly in the following step. ([M+H]+): 327. RT=4.21 min (acetonitrile/water gradient from 30% to 90%—Method B).

Preparation of Example 5:

Example 5 was prepared according to the method described for Example 1, starting with 200 mg of resin (ii), 195 mg of 1-(2-fluoro-3-trifluoromethylphenyl)-3-(3-formylphenyl)-urea (0.6 mmol, 3 eq.) and 66 mg of sodium cyanoborohydride (1 mmol; ~5 eq.). After purification by preparative HPLC, 31.4 mg of product 5 are isolated. (yield=29%). EIMS ([M+H]+): 437. RT=3.33 min (acetonitrile/water gradient from 5% to 100%—Method A).

EXAMPLE 6

4-[(3-{[(3-methoxyphenyl)carbamoyl]amino}benzyl)amino]-1H-pyrazole-3-carboxamide trifluoroacetate

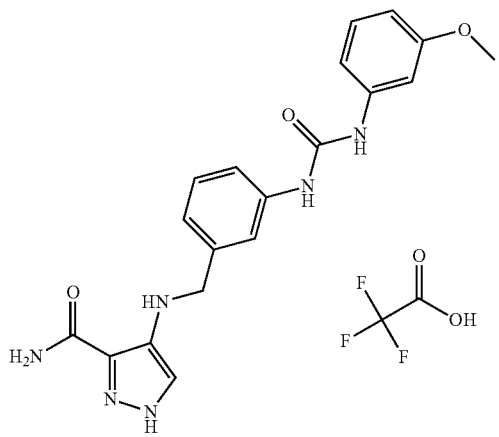 [SMILES: COc1cccc(NC(=O)Nc2cccc(CNc3c[nH]nc3C(N)=O)c2)c1 ; O=C(O)C(F)(F)F]

Preparation of
1-(3-methoxyphenyl)-3-(3-formylphenyl)urea

The product was prepared as described in Example 2, starting with 484 mg of 3-amino-benzaldehyde (4 mmol) (polymerized form) and 597 mg of 3-methoxyphenyl isocyanate (4 mmol) in 4 ml of DCE. 598 mg of crude expected aldehyde are isolated and used directly in the following step. ([M+H]+): 271. RT=5.05 min (acetonitrile/water gradient from 30% to 90%—Method B).

Preparation of Example 6:

Example 6 was prepared according to the method described for Example 1, starting with 200 mg of resin (ii), 162 mg of 1-(3-methoxyphenyl)-3-(3-formylphenyl)urea (0.6 mmol, 3 eq.) and 66 mg of sodium cyanoborohydride (1 mmol; ~5 eq.). After purification by preparative HPLC, 17 mg of product 6 are isolated. (yield=17%). EIMS ([M+H]+): 381. RT=2.47 min (acetonitrile/water gradient from 5% to 100%—Method A).

EXAMPLE 7

4-{[3-({[3-fluoro-5-(trifluoromethyl)phenyl]carbamoyl}amino)benzyl]-amino}-1H-pyrazole-3-carboxamide trifluoroacetate

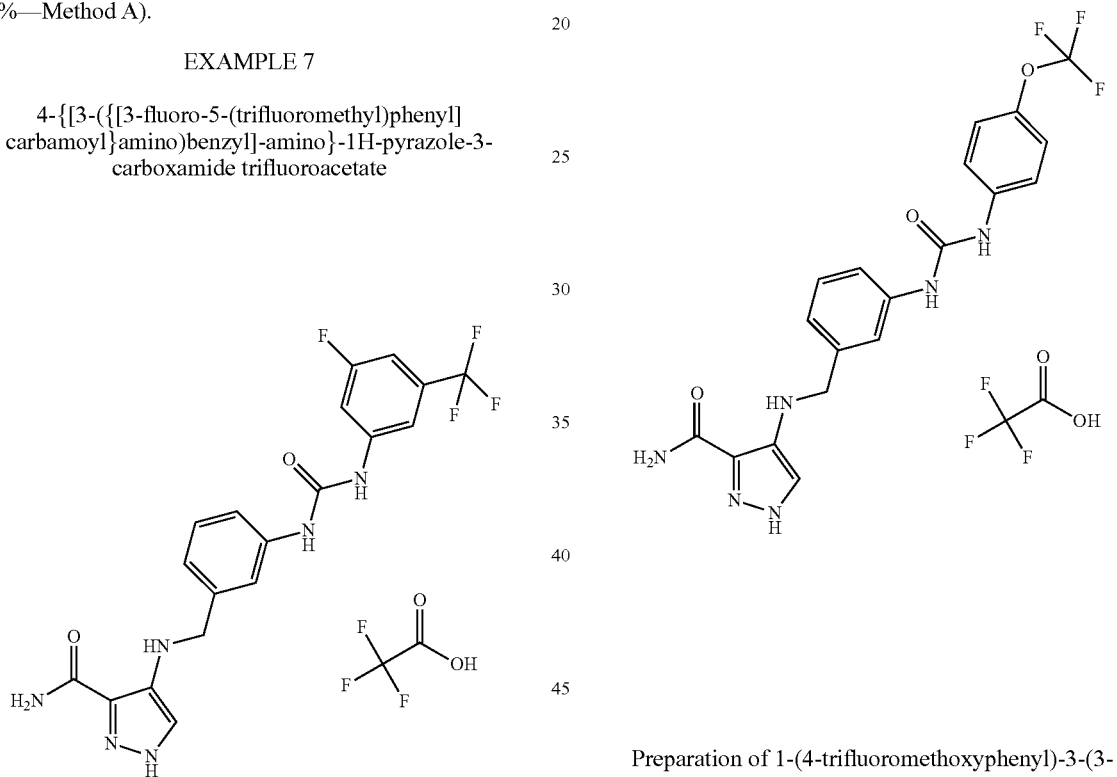

Preparation of 1-(3-fluoro-5-trifluoromethylphenyl)-3-(3-formylphenyl)urea

The product was prepared as described in Example 2, starting with 484 mg of 3-amino-benzaldehyde (4 mmol) (polymerized form) and 597 mg of 3-fluoro-5-trifluoromethylphenyl isocyanate (4 mmol) in 4 ml of DCE. 924 mg of crude expected aldehyde are isolated and used directly in the following step. ([M+H]+): 327. RT=4.48 min (acetonitrile/water gradient from 30% to 90%—Method B).

Preparation of Example 7:

Example 7 was prepared according to the method described for Example 1, starting with 200 mg of resin (ii), 196 mg of 1-(3-fluoro-5-trifluoromethylphenyl)-3-(3-formylphenyl)-urea (0.6 mmol, 3 eq.) and 66 mg of sodium cyanoborohydride (1 mmol; ~5 eq.). After purification by preparative HPLC, 33.6 mg of product 7 are isolated. (yield=31%). EIMS ([M+H]+): 437. RT=3.55 min (acetonitrile/water gradient from 5% to 100%—Method A).

EXAMPLE 8

4-{[3-({[4-(trifluoromethoxy)phenyl]carbamoyl}amino)benzyl]amino}-1H-pyrazole-3-carboxamide trifluoroacetate

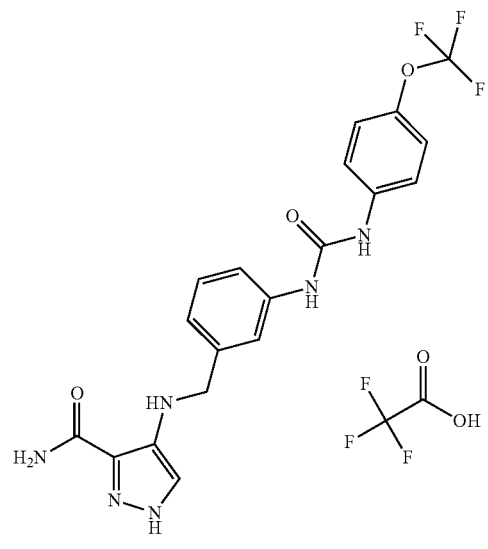 [SMILES: NC(=O)c1n[nH]cc1NCc1cccc(NC(=O)Nc2ccc(OC(F)(F)F)cc2)c1 ; O=C(O)C(F)(F)F]

Preparation of 1-(4-trifluoromethoxyphenyl)-3-(3-formylphenyl)urea

The product was prepared as described in Example 2, starting with 484 mg of 3-amino-benzaldehyde (4 mmol) (polymerized form) and 812 mg of 4-trifluoromethoxyphenyl isocyanate (4 mmol) in 4 ml of DCE. 558 mg of crude expected aldehyde are isolated and used directly in the following step. ([M+H]+): 325. RT=4.13 min (acetonitrile/water gradient from 30% to 90%—Method B).

Preparation of Example 8:

Example 8 was prepared according to the method described for Example 1, starting with 200 mg of resin (ii), 195 mg of 1-(4-trifluoromethoxyphenyl)-3-(3-formylphenyl)urea (0.6 mmol, 3 eq.) and 66 mg of sodium cyanoborohydride (1 mmol; ~5 eq.). After purification by preparative HPLC, 26.3 mg of product 8 are isolated. (yield=24%). EIMS ([M+H]+): 435. RT=3.34 min (acetonitrile/water gradient from 5% to 100%—Method A).

EXAMPLE 9 methyl 3-{[(3-{[(3-carbamoyl-1H-pyrazol-4-yl)amino]methyl}phenyl)-carbamoyl]amino}benzoate trifluoroacetate

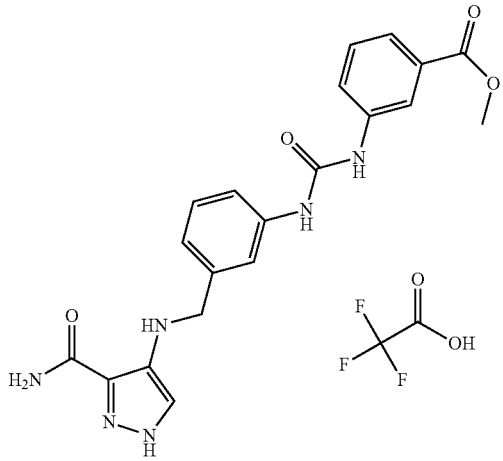 [SMILES: COC(=O)c1cccc(NC(=O)Nc2cccc(CNc3c[nH]nc3C(N)=O)c2)c1 ; O=C(O)C(F)(F)F]

Preparation of 1-(3-methoxycarbonyl)-3-(3-formylphenyl)urea

The product was prepared as described in Example 2, starting with 484 mg of 3-amino-benzaldehyde (4 mmol) (polymerized form) and 812 mg of methyl 3-isocyanobenzoate (4 mmol) in 4 ml of DCE. 695 mg of crude expected aldehyde are isolated and used directly in the following step. ([M+H]+): 299. RT=2.94 min (acetonitrile/water gradient from 30% to 90%—Method B).

Preparation of Example 9:

Example 9 was prepared according to the method described for Example 1, starting with 200 mg of resin (ii), 180 mg of urea (0.6 mmol, 3 eq.) and 66 mg of sodium cyanoborohydride (1 mmol; ~5 eq.). After purification by preparative HPLC, 25.3 mg of product 9 are isolated. (yield=24%). EIMS ([M+H]+): 409. RT=2.67 min (acetonitrile/water gradient from 5% to 100%—Method A).

EXAMPLE 10

4-{[3-({[4-(trifluoromethyl)phenyl]carbamoyl}amino)benzyl]amino}-1H-pyrazole-3-carboxamide trifluoroacetate

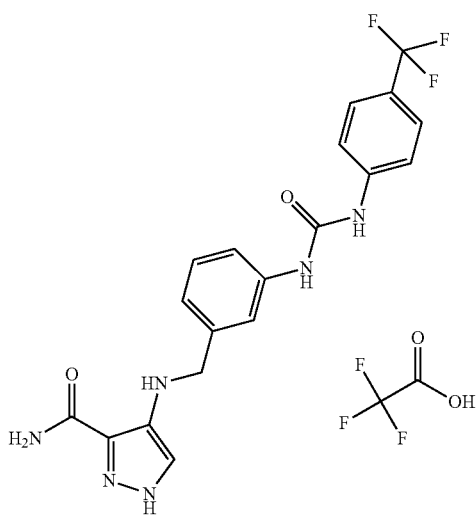 [SMILES: NC(=O)c1n[nH]cc1NCc1cccc(NC(=O)Nc2ccc(C(F)(F)F)cc2)c1 ; O=C(O)C(F)(F)F]

Preparation of 1-(3-formylphenyl)-3-(4-trifluoromethylphenyl)urea

The product was prepared as described in Example 2, starting with 484 mg of 3-amino-benzaldehyde (4 mmol) (polymerized form) and 748 mg of 4-trifluoromethylphenyl isocyanate (4 mmol) in 4 ml of DCE. 896 mg of crude expected aldehyde are isolated and used directly in the following step. ([M+H]+): 309. RT=4.14 min (acetonitrile/water gradient from 30% to 90%—Method B).

Preparation of Example 10:

Example 10 was prepared according to the method described for Example 1, starting with 200 mg of resin (ii), 185 mg of urea (0.6 mmol, 3 eq.) and 66 mg of sodium cyanoborohydride (1 mmol; ~5 eq.). After purification by preparative HPLC, 20.9 mg of product 10 are isolated. (yield=19%). EIMS ([M+H]+): 419. RT=3.33 min (acetonitrile/water gradient from 5% to 100%—Method A).

EXAMPLE 11

4-{[3-({[3-(trifluoromethyl)phenyl]carbamoyl}amino)benzyl]amino}-1H-pyrazole-3-carboxamide trifluoroacetate

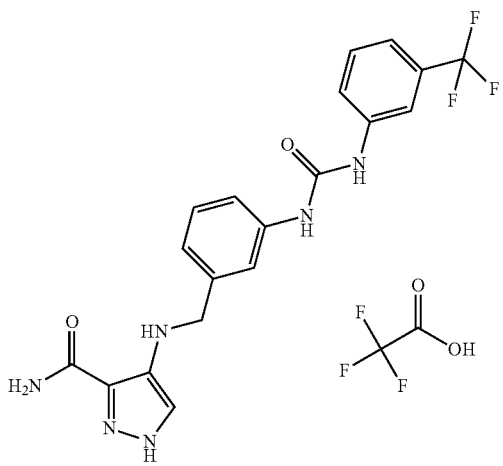 [SMILES: NC(=O)c1n[nH]cc1NCc1cccc(NC(=O)Nc2cccc(C(F)(F)F)c2)c1 ; O=C(O)C(F)(F)F]

Preparation of 1-(3-formylphenyl)-3-(3-trifluoromethylphenyl)urea

The product was prepared as described in Example 2, starting with 484 mg of 3-amino-benzaldehyde (4 mmol) (polymerized form) and 748 mg of 3-trifluoromethylphenyl isocyanate (4 mmol) in 4 ml of DCE. 744 mg of crude expected aldehyde are isolated and used directly in the following step. ([M+H]+): 309. RT=4.04 min (acetonitrile/water gradient from 30% to 90%—Method B).

Preparation of Example 11:

Example 11 was prepared according to the method described for Example 1, starting with 200 mg of resin (ii), 185 mg of urea (0.6 mmol, 3 eq.) and 66 mg of sodium cyanoborohydride (1 mmol; ~5 eq.). After purification by preparative HPLC, 25.9 mg of product 11 are isolated.

EXAMPLE 12

4-{[3-({[2-(trifluoromethyl)phenyl]carbamoyl}amino)benzyl]amino}-1H-pyrazole-3-carboxamide trifluoroacetate

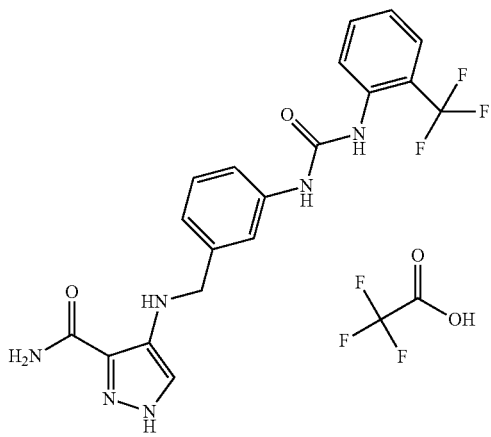 [SMILES: NC(=O)c1n[nH]cc1NCc1cccc(NC(=O)Nc2ccccc2C(F)(F)F)c1 ; O=C(O)C(F)(F)F]

Preparation of 1-(3-formylphenyl)-3-(2-trifluoromethylphenyl)urea

The product was prepared as described in Example 2, starting with 484 mg of 3-amino-benzaldehyde (4 mmol) (polymerized form) and 748 mg of 2-trifluoromethylphenyl isocyanate (4 mmol) in 4 ml of DCE. 744 mg of crude expected aldehyde are isolated and used directly in the following step. ([M+H]+): 309. RT=5.51 min (acetonitrile/water gradient from 30% to 90%—Method B).

Preparation of Example 12:

Example 12 was prepared according to the method described for Example 1, starting with 200 mg of resin (ii), 185 mg of urea (0.6 mmol, 3 eq.) and 66 mg of sodium cyanoborohydride (1 mmol; ~5 eq.). After purification by preparative HPLC, 17.5 mg of product 12 are isolated. (yield=16%). EIMS ([M+H]+): 419. RT=2.64 min (acetonitrile/water gradient from 5% to 100%—Method A).

EXAMPLE 13

4-[(3-{[(3,5-dimethoxyphenyl)carbamoyl]amino}benzyl)amino]-1H-pyrazole-3-carboxamide trifluoroacetate

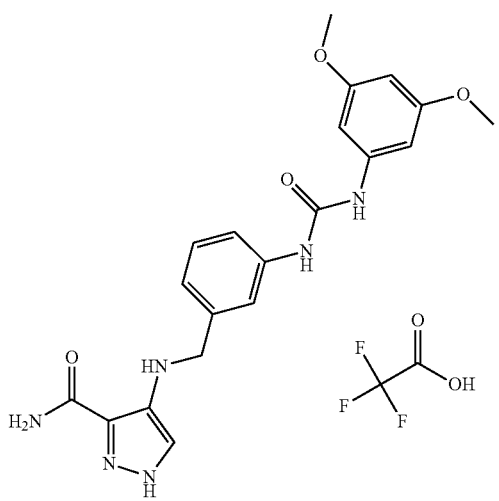 [SMILES: COc1cc(NC(=O)Nc2cccc(CNc3c[nH]nc3C(N)=O)c2)cc(OC)c1 ; O=C(O)C(F)(F)F]

Preparation of 1-(3-formylphenyl)-3-(3,5-dimethoxyphenyl)urea

The product was prepared as described in Example 2, starting with 484 mg of 3-amino-benzaldehyde (4 mmol) (polymerized form) and 717 mg of 3,5-dimethoxyphenyl isocyanate (4 mmol) in 4 ml of DCE. 893 mg of crude expected aldehyde are isolated and used directly in the following step. ([M+H]+): 301. RT=2.99 min (acetonitrile/water gradient from 30% to 90%—Method B).

Preparation of Example 13:

Example 13 was prepared according to the method described for Example 1, starting with 200 mg of resin (ii), 180 mg of urea (0.6 mmol, 3 eq.) and 66 mg of sodium cyanoborohydride (1 mmol; ~5 eq.). After purification by preparative HPLC, 14.9 mg of product 13 are isolated. (yield=14%). EIMS ([M+H]+): 411. RT=4.61 min (acetonitrile/water gradient from 5% to 85%—Method A).

EXAMPLE 14

4-[(3-{[(3-methylphenyl)carbamoyl]amino}benzyl)amino]-1H-pyrazole-3-carboxamide trifluoroacetate

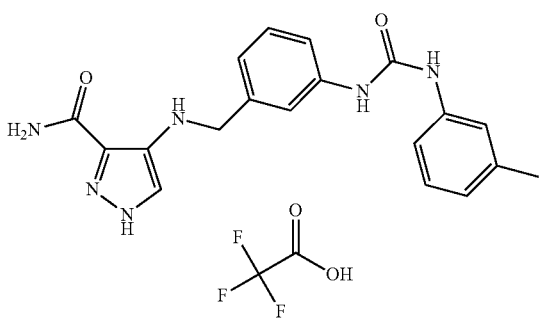 [SMILES: Cc1cccc(NC(=O)Nc2cccc(CNc3c[nH]nc3C(N)=O)c2)c1 ; O=C(O)C(F)(F)F]

Preparation of 1-(3-formylphenyl)-3-(3-tolyl)urea

The product was prepared as described in Example 2, starting with 484 mg of 3-amino-benzaldehyde (4 mmol) (polymerized form) and 533 mg of 3-tolyl isocyanate (4 mmol) in 4 ml of DCE. 629 mg of crude expected aldehyde are isolated and used directly in the following step. ([M+H]+): 255. RT=3.27 min (acetonitrile/water gradient from 30% to 90%—Method B).

Preparation of Example 14:

Example 14 was prepared according to the method described for Example 1, starting with 200 mg of resin (ii), 153 mg of urea (0.6 mmol, 3 eq.) and 66 mg of sodium cyanoborohydride (1 mmol; ~5 eq.). After purification by preparative HPLC, 17 mg of product 14 are isolated. (yield=18%). EIMS ([M+H]+): 365. RT=4.66 min (acetonitrile/water gradient from 5% to 85%—Method B).

EXAMPLE 15

4-[(3-{[(4-methoxyphenyl)carbamoyl]amino}benzyl)amino]-1H-pyrazole-3-carboxamide trifluoroacetate

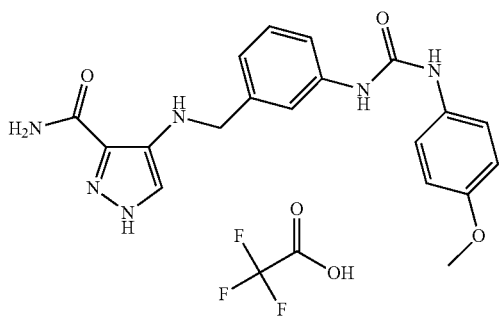 [SMILES: COc1ccc(NC(=O)Nc2cccc(CNc3c[nH]nc3C(N)=O)c2)cc1 ; O=C(O)C(F)(F)F]

Preparation of 1-(3-formylphenyl)-3-(4-methoxyphenyl)urea

The product was prepared as described in Example 2, starting with 484 mg of 3-amino-benzaldehyde (4 mmol) (polymerized form) and 597 mg of 4-methoxyphenyl isocyanate (4 mmol) in 4 ml of DCE. 747 mg of crude expected aldehyde are isolated and used directly in the following step. ([M+H]+): 271. RT=2.53 min (acetonitrile/water gradient from 30% to 90%—Method B).

Preparation of Example 15:

Example 15 was prepared according to the method described for Example 1, starting with 200 mg of resin (ii), 162 mg of urea (0.6 mmol, 3 eq.) and 66 mg of sodium cyanoborohydride (1 mmol; ~5 eq.). After purification by preparative HPLC, 2.6 mg of product 15 are isolated. (yield=3%). EIMS ([M+H]+): 381. RT=4.3 min (acetonitrile/water gradient from 5% to 85%—Method B).

EXAMPLE 16

4-[(3-{[(4-fluorophenyl)carbamoyl]amino}benzyl)amino]-1H-pyrazole-3-carboxamide trifluoroacetate

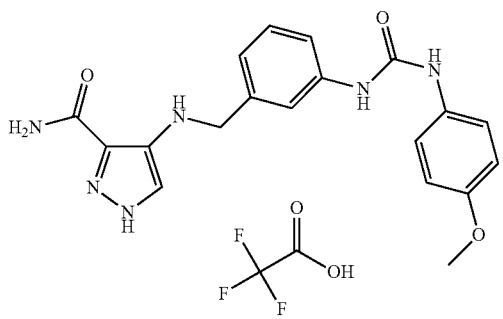 [SMILES: COc1ccc(NC(=O)Nc2cccc(CNc3c[nH]nc3C(N)=O)c2)cc1 ; O=C(O)C(F)(F)F]

Preparation of 1-(3-formylphenyl)-3-(4-fluorophenyl)urea

The product was prepared as described in Example 2, starting with 484 mg of 3-amino-benzaldehyde (4 mmol) (polymerized form) and 548 mg of 4-fluorophenyl isocyanate (4 mmol) in 4 ml of DCE. 760 mg of crude expected aldehyde are isolated and used directly in the following step. ([M+H]+): 259. RT=2.86 min (acetonitrile/water gradient from 30% to 90%—Method B).

Preparation of Example 16:

Example 16 was prepared according to the method described for Example 1, starting with 200 mg of resin (ii), 155 mg of urea (0.6 mmol, 3 eq.) and 66 mg of sodium cyanoborohydride (1 mmol; ~5 eq.). After purification by preparative HPLC, 0.6 mg of product 16 are isolated. (yield=1%). EIMS ([M+H]+): 369. RT=4.44 min (acetonitrile/water gradient from 5% to 85%—Method B).

EXAMPLE 17

4-{[3-({[4-chloro-3-(trifluoromethyl)phenyl]carbamoyl}amino)benzyl]-amino}-1H-pyrazole-3-carboxamide trifluoroacetate

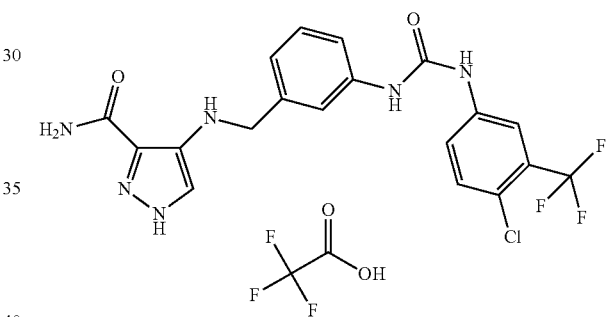

Preparation of 1-(3-formylphenyl)-3-(3-trifluoro-4-chlorophenyl)urea

The product was prepared as described in Example 2, starting with 484 mg of 3-amino-benzaldehyde (4 mmol) (polymerized form) and 886 mg of 4-chloro-3-trifluorofluorophenyl isocyanate (4 mmol) in 4 ml of DCE. 117 mg of crude expected aldehyde are isolated and used directly in the following step. ([M+H]+): 343. RT=4.66 min (acetonitrile/water gradient from 30% to 90%—Method B).

Preparation of Example 17:

Example 17 was prepared according to the method described for Example 1, starting with 200 mg of resin (ii), 206 mg of urea (0.6 mmol, 3 eq.) and 66 mg of sodium cyanoborohydride (1 mmol; ~5 eq.). After purification by preparative HPLC, 7.3 mg of product 17 are isolated. (yield=6%). EIMS ([M+H]+): 453. RT=5.38 min (acetonitrile/water gradient from 5% to 85%—Method B). (yield=24%). EIMS ([M+H]+): 419. RT=3.25 min (acetonitrile/water gradient from 5% to 100%—Method A).

EXAMPLE 18

4-{[3-({[4-(difluoromethoxy)phenyl]carbamoyl}amino)benzyl]amino}-1H-pyrazole-3-carboxamide trifluoroacetate

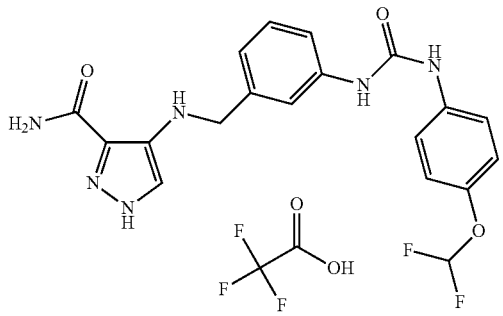 [SMILES: NC(=O)c1n[nH]cc1NCc1cccc(NC(=O)Nc2ccc(OC(F)F)cc2)c1 ; O=C(O)C(F)(F)F]

Preparation of 1-(3-formylphenyl)-3-(4-difluoromethoxyphenyl)urea

The product was prepared as described in Example 2, starting with 484 mg of 3-amino-benzaldehyde (4 mmol) (polymerized form) and 741 mg of 4-difluoromethoxyphenyl isocyanate (4 mmol) in 4 ml of DCE. 840 mg of crude expected aldehyde are isolated and used directly in the following step. ([M+H]+): 307. RT=3.39 min (acetonitrile/water gradient from 30% to 90%—Method B).
Preparation of Example 18:
Example 18 was prepared according to the method described for Example 1, starting with 200 mg of resin (ii), 184 mg of urea (0.6 mmol, 3 eq.) and 66 mg of sodium cyanoborohydride (1 mmol; ~5 eq.). After purification by preparative HPLC, 28.5 mg of product 18 are isolated. (yield=27%). EIMS ([M+H]+): 417. RT=4.9 min (acetonitrile/water gradient from 5% to 85%—Method B).

EXAMPLE 19

4-{[3-({[2-chloro-4-(trifluoromethyl)phenyl]carbamoyl}amino)benzyl]-amino}-1H-pyrazole-3-carboxamide trifluoroacetate

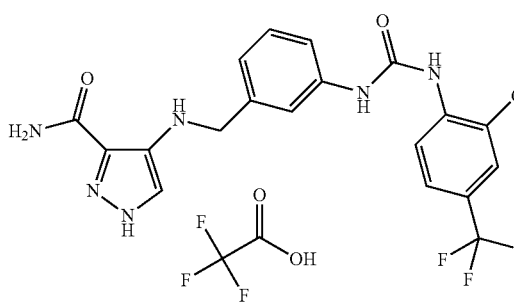

Preparation of 1-(3-formylphenyl)-3-(2-chloro-4-trifluoromethylphenyl)urea

The product was prepared as described in Example 2, starting with 484 mg of 3-amino-benzaldehyde (4 mmol) (polymerized form) and 886 mg of 2-chloro-4-trifluoromethylphenyl isocyanate (4 mmol) in 4 ml of DCE. 1 g of crude expected aldehyde is isolated and used directly in the following step. ([M+H]+): 343. RT=4.66 min (acetonitrile/water gradient from 30% to 90%—Method B).
Preparation of Example 19:
Example 19 was prepared according to the method described for Example 1, starting with 200 mg of resin (ii), 206 mg of urea (0.6 mmol, 3 eq.) and 66 mg of sodium cyanoborohydride (1 mmol; ~5 eq.). After purification by preparative HPLC, 24.3 mg of product 19 are isolated. (yield=22%). EIMS ([M+H]+): 453. RT=5.36 min (acetonitrile/water gradient from 5% to 85%—Method B).

EXAMPLE 20

4-[(3-{[(4-methylphenyl)carbamoyl]amino}benzyl)amino]-1H-pyrazole-3-carboxamide trifluoroacetate

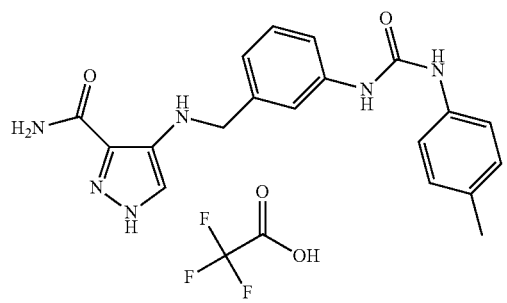

Preparation of 1-(3-formylphenyl)-3-(4-tolyl)urea

The product was prepared as described in Example 2, starting with 484 mg of 3-amino-benzaldehyde (4 mmol) (polymerized form) and 533 mg of 4-tolyl isocyanate (4 mmol) in 4 ml of DCE. 683 mg of crude expected aldehyde are isolated and used directly in the following step. ([M+H]+): 255. RT=3.16 min (acetonitrile/water gradient from 30% to 90%—Method B).
Preparation of Example 20:
Example 20 was prepared according to the method described for Example 1, starting with 200 mg of resin (ii), 153 mg of urea (0.6 mmol, 3 eq.) and 66 mg of sodium cyanoborohydride (1 mmol; ~5 eq.). After purification by preparative HPLC, 15.3 mg of product 20 are isolated. (yield=16%). EIMS ([M+H]+): 365. RT=4.58 min (acetonitrile/water gradient from 5% to 85%—Method B).

EXAMPLE 21

4-[(3-{[(2,5-dimethylphenyl)carbamoyl]amino}benzyl)amino]-1H-pyrazole-3-carboxamide trifluoroacetate

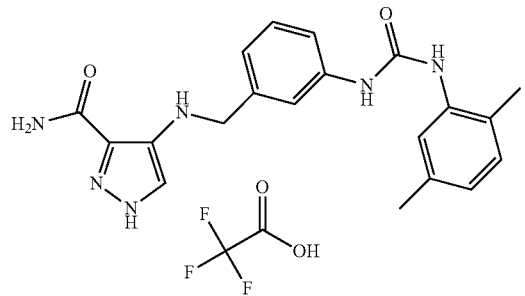

Preparation of 1-(3-formylphenyl)-3-(2,5-dimethylphenyl)urea

The product was prepared as described in Example 2, starting with 484 mg of 3-amino-benzaldehyde (4 mmol) (polymerized form) and 589 mg of 2,5-dimethylphenyl isocyanate (4 mmol) in 4 ml of DCE. 660 mg of crude expected aldehyde are isolated and used directly in the following step. ([M+H]+): 269. RT=3.39 min (acetonitrile/water gradient from 30% to 90%—Method B).

Preparation of Example 21:

Example 21 was prepared according to the method described for Example 1, starting with 200 mg of resin (ii), 161 mg of urea (0.6 mmol, 3 eq.) and 66 mg of sodium cyanoborohydride (1 mmol; ~5 eq.). After purification by preparative HPLC, 26.7 mg of product 21 are isolated. (yield=27%). EIMS ([M+H]+): 379. RT=4.68 min (acetonitrile/water gradient from 5% to 85%—Method B).

EXAMPLE 22

4-[(3-{[(3,4-dimethylphenyl)carbamoyl]amino}benzyl)amino]-1H-pyrazole-3-carboxamide trifluoroacetate

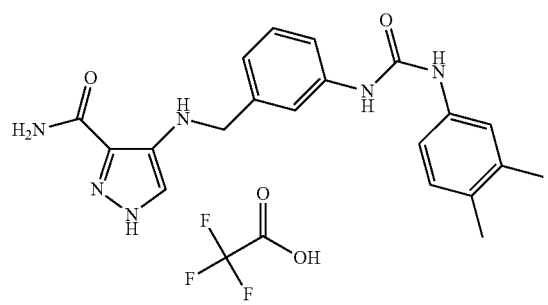

Preparation of 1-(3-formylphenyl)-3-(3,4-dimethylphenyl)urea

The product was prepared as described in Example 2, starting with 484 mg of 3-amino-benzaldehyde (4 mmol) (polymerized form) and 589 mg of 3,4-dimethylphenyl isocyanate (4 mmol) in 4 ml of DCE. 621 mg of crude expected aldehyde are isolated and used directly in the following step. ([M+H]+): 269. RT=3.55 min (acetonitrile/water gradient from 30% to 90%—Method B).

Preparation of Example 22:

Example 22 was prepared according to the method described for Example 1, starting with 200 mg of resin (ii), 161 mg of urea (0.6 mmol, 3 eq.) and 66 mg of sodium cyanoborohydride (1 mmol; ~5 eq.). After purification by preparative HPLC, 32 mg of product 22 are isolated. (yield=32%). EIMS ([M+H]+): 379. RT=4.8 min (acetonitrile/water gradient from 5% to 85%—Method B).

EXAMPLE 23

4-[(3-{[(2-methylphenyl)carbamoyl]amino}benzyl)amino]-1H-pyrazole-3-carboxamide trifluoroacetate

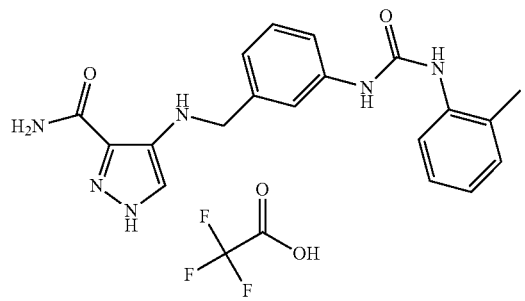

Preparation of 1-(3-formylphenyl)-3-(2-tolyl)urea

The product was prepared as described in Example 2, starting with 484 mg of 3-amino-benzaldehyde (4 mmol) (polymerized form) and 533 mg of 2-tolyl isocyanate (4 mmol) in 4 ml of DCE. 621 mg of crude expected aldehyde are isolated and used directly in the following step. ([M+H]+): 255. RT=5.14 min (acetonitrile/water gradient from 30% to 90%—Method B).

Preparation of Example 23:

Example 23 was prepared according to the method described for Example 1, starting with 200 mg of resin (ii), 153 mg of urea (0.6 mmol, 3 eq.) and 66 mg of sodium cyanoborohydride (1 mmol; ~5 eq.). After purification by preparative HPLC, 16.7 mg of product 23 are isolated. (yield=17%). EIMS ([M+H]+): 365. RT=4.5 min (acetonitrile/water gradient from 5% to 85%—Method B).

EXAMPLE 24

4-[(3-{[(3-ethylphenyl)carbamoyl]amino}benzyl)amino]-1H-pyrazole-3-carboxamide trifluoroacetate

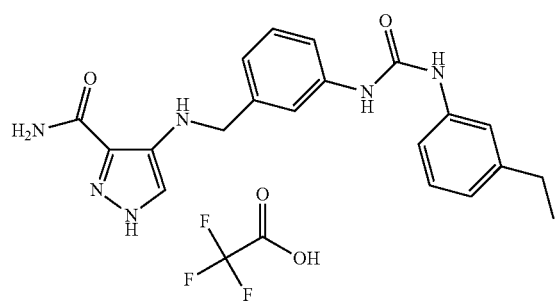

Preparation of 1-(3-formylphenyl)-3-(3-ethylphenyl)urea

The product was prepared as described in Example 2, starting with 484 mg of 3-amino-benzaldehyde (4 mmol) (polymerized form) and 589 mg of 3-ethylphenyl isocyanate (4 mmol) in 4 ml of DCE. 732 mg of crude expected aldehyde are isolated and used directly in the following step. ([M+H]+): 255. RT=5.51 min (acetonitrile/water gradient from 30% to 90%—Method B).

Preparation of Example 24:

Example 24 was prepared according to the method described for Example 1, starting with 200 mg of resin (ii), 160 mg of urea (0.6 mmol, 3 eq.) and 66 mg of sodium cyanoborohydride (1 mmol; ~5 eq.). After purification by preparative HPLC, 12.2 mg of product 24 are isolated. (yield=12%). EIMS ([M+H]+): 365. RT=4.5 min (acetonitrile/water gradient from 5% to 85%—Method B).

EXAMPLE 25

4-{[3-({[3,5-bis(trifluoromethyl)phenyl]carbamoyl}amino)benzyl]-amino}-1H-pyrazole-3-carboxamide trifluoroacetate

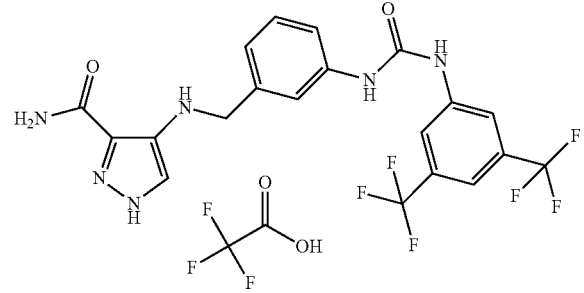

Preparation of 1-(3-formylphenyl)-3-(3,5-bis-trifluoromethylphenyl)urea

The product was prepared as described in Example 2, starting with 484 mg of 3-amino-benzaldehyde (4 mmol) (polymerized form) and 1.02 g of 3,5-bis-trifluoromethylphenyl isocyanate (4 mmol) in 4 ml of DCE. 489 mg of crude expected aldehyde are isolated and used directly in the following step. ([M+H]+): 377. RT=5.05 min (acetonitrile/water gradient from 30% to 90%—Method B).

Preparation of Example 25:

Example 25 was prepared according to the method described for Example 1, starting with 200 mg of resin (ii), 225 mg of urea (0.6 mmol, 3 eq.) and 66 mg of sodium cyanoborohydride (1 mmol; ~5 eq.). After purification by preparative HPLC, 3.3 mg of product 25 are isolated. (yield=4%). EIMS ([M+H]+): 365. RT=4.5 min (acetonitrile/water gradient from 5% to 85%—Method B).

EXAMPLE 26

4-[(3-{[(3-fluorophenyl)carbamoyl]amino}benzyl)amino]-1H-pyrazole-3-carboxamide trifluoroacetate

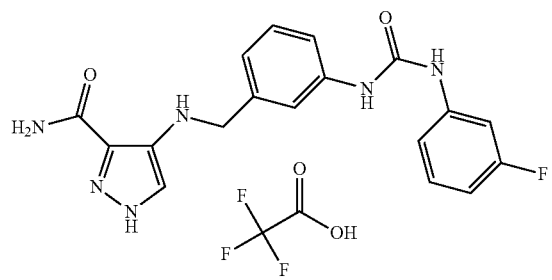 [SMILES: NC(=O)c1n[nH]cc1NCc1cccc(NC(=O)Nc2cccc(F)c2)c1 ; O=C(O)C(F)(F)F]

Preparation of 1-(3-formylphenyl)-3-(3-fluorophenyl)urea

The product was prepared as described in Example 2, starting with 484 mg of 3-amino-benzaldehyde (4 mmol) (polymerized form) and 548 mg of 3-fluorophenyl isocyanate (4 mmol) in 4 ml of DCE. 723 mg of crude expected aldehyde are isolated and used directly in the following step. ([M+H]+): 259. RT=4.04 min (acetonitrile/water gradient from 30% to 90%—Method B).

Preparation of Example 26:

Example 26 was prepared according to the method described for Example 1, starting with 200 mg of resin (ii), 155 mg of urea (0.6 mmol, 3 eq.) and 66 mg of sodium cyanoborohydride (1 mmol; ~5 eq.). After purification by preparative HPLC, 23.5 mg of product 26 are isolated. (yield=25%). EIMS ([M+H]+): 369. RT=4.7 min (acetonitrile/water gradient from 5% to 85%—Method B).

EXAMPLE 27

4-[(3-{[(2-methoxy-5-methylphenyl)carbamoyl]amino}benzyl)amino]-1H-pyrazole-3-carboxamide trifluoroacetate

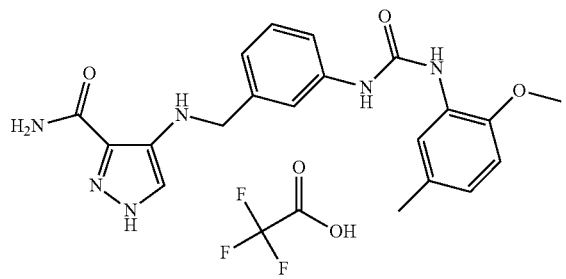 [SMILES: COc1ccc(C)cc1NC(=O)Nc1cccc(CNc2c[nH]nc2C(N)=O)c1 ; O=C(O)C(F)(F)F]

Preparation of 1-(3-formylphenyl)-3-(2-methoxy-5-methylphenyl)urea

The product was prepared as described in Example 2, starting with 484 mg of 3-amino-benzaldehyde (4 mmol) (polymerized form) and 653 mg of 2-methoxy-5-methylphenyl isocyanate (4 mmol) in 4 ml of DCE. 797 mg of crude expected aldehyde are isolated and used directly in the following step. ([M+H]+): 285. RT=2.94 min (acetonitrile/water gradient from 30% to 90%—Method B).

Preparation of Example 27:

Example 27 was prepared according to the method described for Example 1, starting with 200 mg of resin (ii), 170 mg of urea (0.6 mmol, 3 eq.) and 66 mg of sodium cyanoborohydride (1 mmol; ~5 eq.). After purification by preparative HPLC, 20 mg of product 27 are isolated. (yield=25%). EIMS ([M+H]+): 395. RT=5 min (acetonitrile/water gradient from 5% to 85%—Method B).

EXAMPLE 28

4-[(3-{[(2,5-dimethoxyphenyl)carbamoyl]amino}benzyl)amino]-1H-pyrazole-3-carboxamide trifluoroacetate

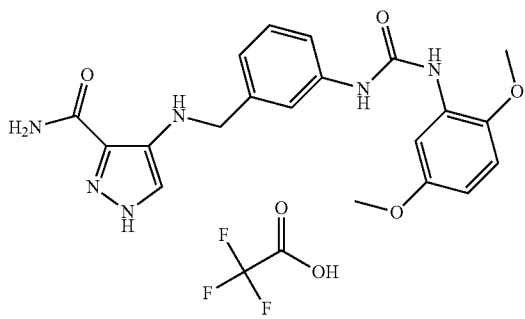 [SMILES: COc1ccc(OC)c(NC(=O)Nc2cccc(CNc3c[nH]nc3C(N)=O)c2)c1 ; O=C(O)C(F)(F)F]

Preparation of 1-(3-formylphenyl)-3-(2,5-dimethoxyphenyl)urea

The product was prepared as described in Example 2, starting with 484 mg of 3-amino-benzaldehyde (4 mmol) (polymerized form) and 717 mg of 2,5-dimethoxyphenyl isocyanate (4 mmol) in 4 ml of DCE. 853 mg of crude expected aldehyde are isolated and used directly in the following step. ([M+H]+): 301. RT=4.14 min (acetonitrile/water gradient from 30% to 90%—Method B).

Preparation of Example 28:

Example 28 was prepared according to the method described for Example 1, starting with 200 mg of resin (ii), 170 mg of urea (0.6 mmol, 3 eq.) and 66 mg of sodium cyanoborohydride (1 mmol; ~5 eq.). After purification by preparative HPLC, 11.8 mg of product 28 are isolated. (yield=12%). EIMS ([M+H]+): 411. RT=4.72 min (acetonitrile/water gradient from 5% to 85%—Method B).

EXAMPLE 29

4-{[3-({[3-chloro-4-(difluoromethoxyphenyl]carbamoyl}amino)benzyl]-amino}-1H-pyrazole-3-carboxamide trifluoroacetate

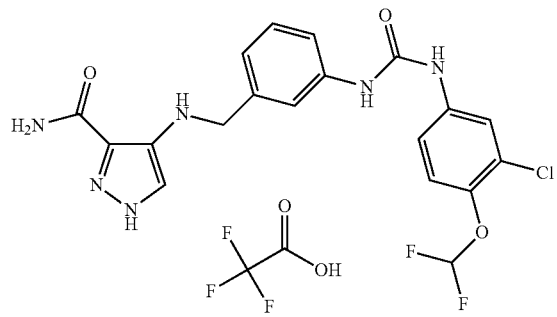 [SMILES: NC(=O)c1n[nH]cc1NCc1cccc(NC(=O)Nc2ccc(OC(F)F)c(Cl)c2)c1 ; O=C(O)C(F)(F)F]

Preparation of 1-(3-formylphenyl)-3-(3-chloro-4-difluoromethoxyphenyl)urea

The product was prepared as described in Example 2, starting with 484 mg of 3-amino-benzaldehyde (4 mmol) (polymerized form) and 878 mg of 3-chloro-4-difluoromethoxyphenyl isocyanate (4 mmol) in 4 ml of DCE. 936 mg of crude expected aldehyde are isolated and used directly in the following step. ([M+H]+): 341. RT=4.21 min (acetonitrile/water gradient from 30% to 90%—Method B).

Preparation of Example 29:

Example 29 was prepared according to the method described for Example 1, starting with 200 mg of resin (ii), 204 mg of urea (0.6 mmol, 3 eq.) and 66 mg of sodium cyanoborohydride (1 mmol; ~5 eq.). After purification by preparative HPLC, 8.3 mg of product 29 are isolated. (yield=7%). EIMS ([M+H]+): 451. RT=5.36 min (acetonitrile/water gradient from 5% to 85%—Method B).

EXAMPLE 30

4-[(3-{[(2,5-difluorophenyl)carbamoyl]amino}benzyl)amino]-1H-pyrazole-3-carboxamide trifluoroacetate

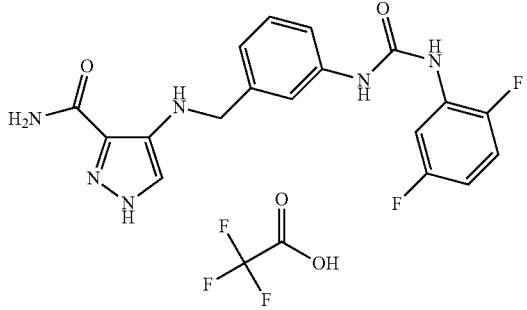 [SMILES: NC(=O)c1n[nH]cc1NCc1cccc(NC(=O)Nc2cc(F)ccc2F)c1 ; O=C(O)C(F)(F)F]

Preparation of 1-(3-formylphenyl)-3-(2,5-difluorophenyl)urea

The product was prepared as described in Example 2, starting with 484 mg of 3-amino-benzaldehyde (4 mmol) (polymerized form) and 620 mg of 2,5-difluorophenyl isocyanate (4 mmol) in 4 ml of DCE. 952 mg of crude expected aldehyde are isolated and used directly in the following step. ([M+H]+): 277. RT=4.13 min (acetonitrile/water gradient from 30% to 90%—Method B).

Preparation of Example 30:

Example 30 was prepared according to the method described for Example 1, starting with 200 mg of resin (ii), 167 mg of urea (0.6 mmol, 3 eq.) and 66 mg of sodium cyanoborohydride (1 mmol; ~5 eq.). After purification by preparative HPLC, 14.1 mg of product 30 are isolated. (yield=14%). EIMS ([M+H]+): 387. RT=4.82 min (acetonitrile/water gradient from 5% to 85%—Method B).

EXAMPLE 31

4-{[3-({[4-methyl-3-(trifluoromethyl)phenyl]carbamoyl}amino)benzyl]-amino}-1H-pyrazole-3-carboxamide trifluoroacetate

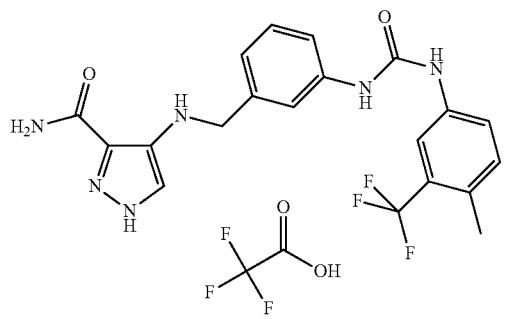 [SMILES: Cc1ccc(NC(=O)Nc2cccc(CNc3c[nH]nc3C(N)=O)c2)cc1C(F)(F)F ; O=C(O)C(F)(F)F]

Preparation of 1-(3-formylphenyl)-3-(4-methyl-3-trifluoromethylphenyl)urea

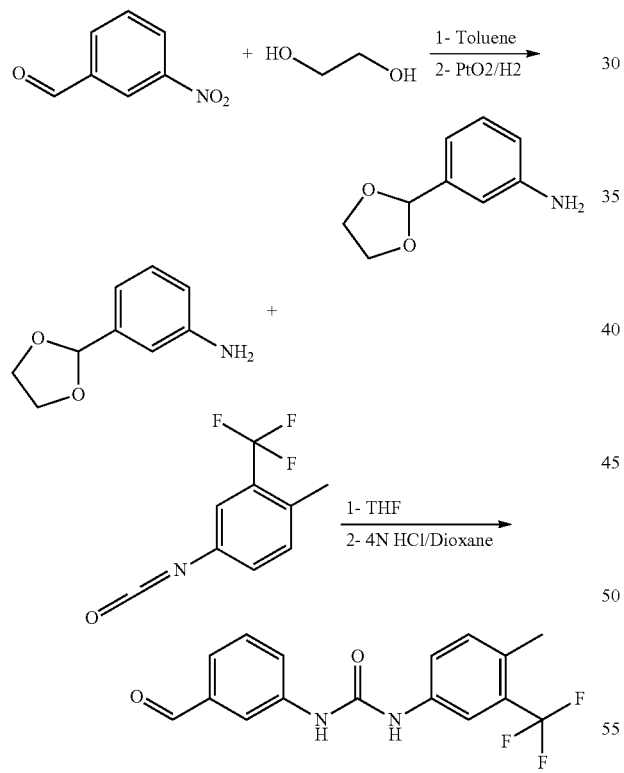

The urea was prepared in the following manner: 3 g of 3-nitrobenzaldehyde (20 mmol), 3.4 ml of ethylene glycol (60 mmol) and 0.3 g of para-toluenesulfonic acid dissolved in 250 ml of toluene are boiled for 4 hours and the mixture is then poured into 100 ml of saturated sodium bicarbonate solution and extracted with twice 50 ml of ethyl acetate. The combined organic phases are washed with water, dried over sodium sulfate and evaporated under vacuum. The crude product is directly hydrogenated in 20 ml of THF in the presence of 160 mg of platinum oxide in a Parr flask. After hydrogenation for 4 hours at room temperature, the reaction mixture is filtered through Celite. To avoid any degradation, the aniline obtained is left dissolved in the THF at a concentration of 10 mmol/20 ml and used in this form for the formation of the urea.

2 ml of the aniline solution (1 mmol) are treated with 200 mg of 4-methyl-3-trifluoromethylphenyl isocyanate for 4 hours at room temperature. The mixture is poured into 100 ml of 10% HCl solution and extracted with twice 50 ml of ethyl acetate. The combined organic phases are washed with water, dried over sodium sulfate and evaporated under vacuum. 320 mg of expected product are isolated in the form of a solid. (quantitative yield) EIMS ([M+H]+): 323. RT=4.37 min (acetonitrile/water gradient from 30% to 90%—Method B).

Preparation of Example 31:

Example 31 was prepared according to the method described for Example 1, starting with 200 mg of resin (ii), 193 mg of urea (0.6 mmol, 3 eq.) and 66 mg of sodium cyanoborohydride (1 mmol; ~5 eq.). After purification by preparative HPLC, 36.7 mg of product 31 are isolated. (yield=34%). EIMS ([M+H]+): 433. RT=4.64 min (acetonitrile/water gradient from 5% to 85%—Method B).

EXAMPLE 32 methyl 4-{[3-({[2-fluoro-5-(trifluoromethyl)phenyl]carbamoyl}amino)-benzyl]amino}-1H-pyrazole-3-carboxylate trifluoroacetate

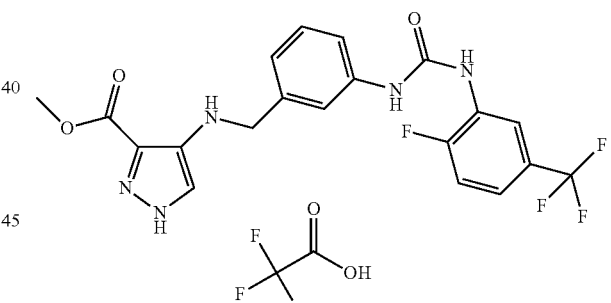

Compound 32 was prepared by direct reductive amination of methyl 4-amino-3-pyrazolecarboxylate. A solution of 44 mg of methyl 4-amino-3-pyrazolecarboxylate (0.31 mmol) and 100 mg of 1-(2-fluoro-5-trifluoromethylphenyl)-3-(3-formylphenyl)urea (see Example 2) in a mixture of 0.6 ml of DCE and 0.5 ml of DMF is treated with a solution of 59 mg of sodium cyanoborohydride in 0.5 ml of methanol and 0.05 ml of acetic acid. The mixture is stirred for 2 hours at 80° C. and then cooled and poured into 20 ml of water. The mixture is extracted with twice 20 ml of ethyl acetate. The combined organic phases are washed with water, dried over sodium sulfate and evaporated under vacuum. After purification by preparative HPLC, 20.8 mg of product 32 are isolated. (yield=12%). EIMS ([M+H]+): 452. RT=5.52 min (acetonitrile/water gradient from 5% to 85%—Method B).

EXAMPLE 33

4-(1-{3-[3-(2-fluoro-5-trifluoromethylphenyl)ureido]phenylethylamino}-1H-pyrazole-3-carboxamide trifluoroacetate (1:1)

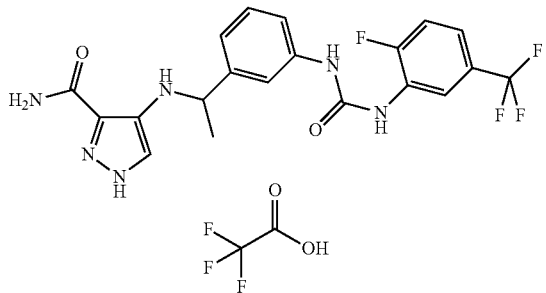 [SMILES: CC(Nc1c[nH]nc1C(N)=O)c1cccc(NC(=O)Nc2cc(C(F)(F)F)ccc2F)c1 ; O=C(O)C(F)(F)F]

Preparation of 1-(3-acetylphenyl)-3-(2-fluoro-5-trifluoromethylphenyl)urea

A mixture of 181 mg of 3-aminoacetophenone (1.34 mmol) and 275 mg of 2-fluoro-5-trifluoromethylphenyl isocyanate (1.34 mmol) in 1 ml of THF is stirred at room temperature for 1 hour and then evaporated. The solid is taken up in ether and filtered off. 307 mg of expected ketone (yield=69%) are isolated in an LC/MS purity of 87%. The crude product is used directly in the following step. ([M+H]+): 341. Ret. time: 6.06 min (Method A).

Preparation of Example 33:

450 mg of resin I (0.45 mmol) are swollen in 2 ml of DCE, and 307 mg of 1-(3-acetylphenyl)-3-(2-fluoro-5-trifluoromethylphenyl)urea (0.9 mmol; 2 eq.) dissolved in 2 ml of DMF are then added, followed by 149 mg of sodium cyanoborohydride (2.25 mmol; 5 eq.). The mixture is treated in a CEM Discover microwave oven at 100° C. for 10 minutes (power 90). The resin is then washed successively with twice 2 ml of MeOH, three times 2 ml of dichloromethane, twice 2 ml of MeOH and three times 2 ml of dichloromethane. The product is cleaned by treating the resin with 4 ml of a 50/50 trifluoroacetic acid/dichloromethane solution. The solution is evaporated and the crude product obtained is purified directly by HPLC preparative. After freeze-drying, 13.5 mg of expected product are obtained (white solid, yield=5%). ([M+H]+): 451. RT: 4.77 min (Method A).

EXAMPLE 34

4-({3-[3-(2-fluoro-5-trifluoromethylphenyl)ureido]benzyl}methyl-amino)-1H-pyrazole-3-carboxamide

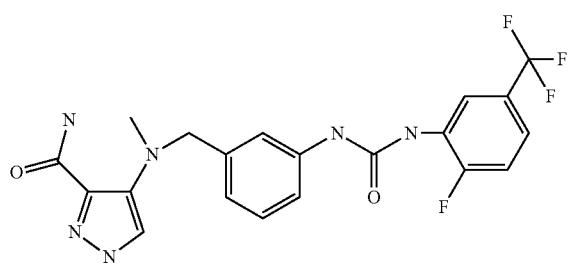 [SMILES: CN(Cc1cccc(NC(=O)Nc2cc(C(F)(F)F)ccc2F)c1)c1c[nH]nc1C(N)=O]

A solution of 0.14 ml of 1-fluoro-2-isocyanato-4-trifluoromethylbenzene is added at 20° C. to a solution of 0.25 g of 4-[(3-aminobenzyl)methylamino]-1H-pyrazole-3-carboxamide in 25 ml of anhydrous THF. The reaction medium is stirred for 12 hours at 20° C. and then diluted with 100 ml of ethyl acetate. The organic phase is washed with 50 ml of distilled water, and is then separated out by settling of the phases, dried over magnesium sulfate and evaporated to dryness under reduced pressure. The residue obtained is chromatographed on a column of silica (15 g of Merck cartridge silica with a particle size of 15 to 45 μm, column diameter 2.2 cm, 5 ml fractions, flow rate of 10 ml/min, eluent 95/5 dichloromethane/methanol—by volume). Fractions 35 to 95 are combined and evaporated to dryness under reduced pressure. 0.02 g of 4-({3-[3-(2-fluoro-5-trifluoromethylphenyl)ureido]benzyl}methylamino)-1H-pyrazole-3-carboxamide is obtained in the form of a solid. ([M+H]+): 451). RT: 3.55 min (Method A).

4-[(3-Aminobenzyl)methylamino]-1H-pyrazole-3-carboxamide is obtained in the following manner:

3.6 g of tin chloride dihydrate are added portionwise at 20° C. to a solution of 1.26 g of 4-[methyl(3-nitrobenzyl)amino]-1H-pyrazole-3-carboxamide in 90 ml of absolute ethanol. The reaction medium is stirred for 15 hours at 20° C., and brought to dryness under reduced pressure. The residue is taken up in 500 ml of a 90/10 methylene chloride/methanol mixture (by volume) and 500 ml of saturated potassium hydrogen carbonate solution. This medium is stirred at 20° C. for 2 hours and then filtered. The solid obtained after filtration is extracted twice with a mixture of 100 ml of 90/10 methylene chloride/methanol (by volume), and the liquid phases are combined and separated by settling. The aqueous phase is extracted with twice 200 ml of methylene chloride, and the organic phases are combined, washed with 300 ml of saturated aqueous sodium chloride solution, dried over sodium sulfate, filtered and evaporated to dryness under reduced pressure. 0.6 g of 4-[(3-aminobenzyl)methylamino]-1H-pyrazole-3-carboxamide is obtained in the form of a cream-colored foam. ([M+H]+): 246). RT: 0.3 min (Method A).

4-[Methyl(3-nitrobenzyl)amino]-1H-pyrazole-3-carboxamide is prepared in the following manner:

4.45 g of para-toluenesulfonic acid monohydrate are added to a solution of 2.49 g of 4-[methyl(3-nitrobenzyl)amino]-1H-pyrazole-3-carboxylic acid 2,4-dimethoxybenzylamide in 30 ml of toluene, and the reaction medium is then heated at the reflux temperature of the toluene for 17 hours. After cooling the reaction medium to room temperature, 15 ml of methanol are added, followed by 700 ml of ethyl acetate and finally 300 ml of distilled water. The pH of this medium is adjusted to a value of 11 by adding 100 ml of aqueous 1N sodium hydroxide solution. This solution is filtered, the solid is extracted twice with 30 ml of ethyl acetate, and the liquid phases are combined and then separated by settling of the phases. The aqueous phase is extracted with twice 200 ml of methylene chloride, the organic phases are combined, washed with 300 ml of saturated aqueous sodium chloride solution, dried over magnesium sulfate, filtered and evaporated to dryness under reduced pressure. 1.41 g of 4-[methyl(3-nitrobenzyl)amino]-1H-pyrazole-3-carboxamide are obtained in the form of a beige-colored solid melting at 166° C. ([M+H]+): 276). RT: 2.61 min (Method A).

4-[Methyl(3-nitrobenzyl)amino]-1H-pyrazole-3-carboxylic acid 2,4-dimethoxybenzylamide is obtained in the following manner:

A solution of 1.61 g of 4-(3-nitrobenzylamino)-1H-pyrazole-3-carboxylic acid 2,4-dimethoxybenzylamide, 1.25 g of paraformaldehyde and 0.94 g of anhydrous magnesium sulfate in 70 ml of glacial acetic acid is stirred at room temperature for 4 hours. 1.23 g of sodium cyanoborohydride are then added portionwise to this solution. The reaction medium is stirred for 2 hours at room temperature, and then poured onto 300 ml of aqueous 5N sodium hydroxide solution and 120 g of crushed ice, the pH being adjusted to 11. 300 ml of saturated sodium chloride solution are then added. This solution is filtered and the solid is washed three times with 60 ml of distilled water. The solid thus collected is air-dried. 1.51 g of 4-[methyl(3-nitrobenzyl)amino]-1H-pyrazole-3-carboxylic acid 2,4-dimethoxybenzylamide are obtained in the form of a pale yellow solid. ([M+H]+): 426). RT: 3.87 min (Method A).

4-(3-Nitrobenzylamino)-1H-pyrazole-3-carboxylic acid 2,4-dimethoxybenzylamide is obtained in the following manner:

8.2 g of 3-nitrobenzaldehyde and 5.9 g of anhydrous magnesium sulfate are added to a solution of 15.43 g of 4-amino-1H-pyrazole-3-carboxylic acid-2,4-dimethoxybenzylamide hydrochloride and 7.01 g of diisopropylethylamine in 490 ml of anhydrous tetrahydrofuran. The reaction medium is refluxed for 1 hour 30 minutes, allowed to cool to 20° C. and then cooled to 5° C. using an ice bath. 15.5 g of sodium cyanoborohydride are added portionwise to the cream-colored suspension obtained. The reaction medium is stirred for 5 minutes at 5° C. and then allowed to warm to room temperature. It is left stirring at room temperature for 20 hours. The cloudy orange-brown solution obtained is poured into 1500 ml of distilled water. 1000 ml of dichloromethane are added to the light-brown milky solution obtained. After stirring, followed by separating out the chloromethylene phase by settling, the aqueous phase is re-extracted with twice 500 ml of dichloromethane. The organic phases are combined and then washed with 500 ml of saturated aqueous sodium chloride solution, dried over magnesium sulfate, filtered through paper and then brought to dryness on a rotary evaporator (temp. 40° C. P: 15 mbar). 27.19 g of a tacky yellow solid are obtained, which product is recrystallized from 360 ml of refluxing acetonitrile. A first crop of 7.7 g of 4-(3-nitrobenzylamino)-1H-pyrazole-3-carboxylic acid 2.4-dimethoxybenzylamide is obtained in the form of a yellow solid.

The acetonitrile filtrate is recovered and then brought to dryness on a rotary evaporator (temp. 40° C. P: 15 mbar). 19.7 g of a tacky ochre-colored mass are obtained, which product is triturated at 20° C. with 50 ml of acetonitrile for 1 hour. The suspension obtained is filtered through a No. 3 sinter funnel and washed with twice 15 ml of acetonitrile. After drying in air and then in a Heraeus oven (temp. 40° C. P: 0.2 mbar), a second crop of 6.59 g of 4-(3-nitrobenzylamino)-1H-pyrazole-3-carboxylic acid 2,4-dimethoxybenzylamide is obtained in the form of a yellow solid.

([M+H]+): 412). RT: 3.93 min (Method A).

4-Amino-1H-pyrazole-3-carboxylic acid 2,4-dimethoxybenzylamide is prepared in the following manner:

27.64 g of tin chloride dihydrate are added portionwise to a suspension of 10.72 g of 4-nitro-1H-pyrazole-3-carboxylic acid 2,4-dimethoxybenzylamide in 600 ml of absolute ethanol. The reaction medium is stirred for 48 hours at 20° C. The clear brown solution obtained is brought to dryness on a rotary evaporator. The clear brown foam obtained is taken up in 700 ml of a 90/10 by volume a mixture of methylene chloride/methanol. 700 ml of saturated aqueous sodium hydrogen carbonate solution are added to the brown solution obtained. The cream-colored suspension obtained is stirred for 1 hour at room temperature. 30 g of Clarcel Flo are added to the suspension and the mixture is then stirred for 10 minutes at room temperature. The resulting mixture is filtered and the filter cake is washed with twice 250 ml of a 90/10 by volume a mixture of methylene chloride/methanol. The solid is drained by suction and the filtrate is recovered and then transferred into a separating funnel. The chloromethylene phase is separated out by settling and the aqueous phase is then re-extracted with twice 250 ml of dichloromethane. The organic phases are combined and then dried over magnesium sulfate, filtered through paper and then brought to dryness on a rotary evaporator. 8.53 g of 4-amino-1H-pyrazole-3-carboxylic acid 2,4-dimethoxybenzylamide are obtained in the form of a pale pink solid. ([M+H]+): 277). RT: 2.36 min (Method A).

4-Nitro-1H-pyrazole-3-carboxylic acid 2,4-dimethoxybenzylamide is obtained in the following manner:

23 g of 2,4-dimethoxybenzylamine and then 20.04 g of 98% 4-nitro-3-pyrazolecarboxylic acid are added to a solution of 28.76 g of 1-(3-dimethylaminopropyl)-3-ethylcarbodiimide hydrochloride and 20.27 g of 1-hydroxybenzotriazole in 100 ml of dimethylformamide. The reaction medium is stirred for at room temperature for 20 hours. The clear yellow solution obtained is then poured into 1000 ml of distilled water. A white suspension is obtained, which is left at room temperature for 1 hour. The suspension is filtered and the filter cake is washed with three times 250 ml of distilled water. The solid obtained is drained by suction and dried in air and then in a Heraeus oven under vacuum (temp. 40° C. P: 0.2 mbar). 40.65 g of a white solid are obtained, which product is triturated in 750 ml of refluxing isopropanol for 20 minutes. The suspension obtained is cooled in a bath of water+ice for 2 hours, and then filtered off. The filter cake is washed with twice 100 ml of isopropanol and then twice 100 ml of isopropyl ether. The solid obtained is dried in air and then in a Heraeus oven (temp. 40° C. P: 0.2 mbar). 32.16 g of 4-nitro-1H-pyrazole-3-carboxylic acid 2,4-dimethoxybenzylamide are obtained in the form of a white solid melting at 204° C. ([M+H]+): 307). RT: 3.12 min

EXAMPLE 35

4-(ethyl-{3-[3-(2-fluoro-5-trifluoromethyl phenyl)ureido]benzyl}amino)-1H-pyrazole-3-carboxamide

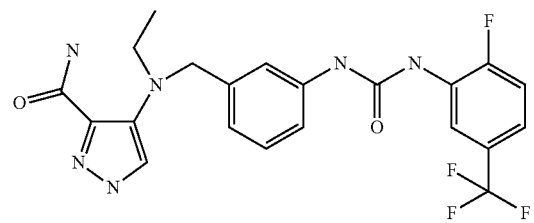 [SMILES: CCN(Cc1cccc(NC(=O)Nc2cc(C(F)(F)F)ccc2F)c1)c1c[nH]nc1C(N)=O]

4-(Ethyl-{3-[3-(2-fluoro-5-trifluoromethylphenyl)ureido]benzyl}amino)-1H-pyrazole-3-carboxamide is prepared by condensing 1-fluoro-2-isocyanato-4-trifluoromethylbenzene with 4-[(3-aminobenzyl)ethylamino]-1H-pyrazole-3-carboxamide according to the procedure described in Example 34, the latter derivative itself being prepared from 4-[(3-nitrobenzyl)ethylamino]-1H-pyrazole-3-carboxamide according to the procedure also described in Example 34.

4-[(3-Nitrobenzyl)ethylamino]-1H-pyrazole-3-carboxamide is obtained in the following manner:

A solution of 2.2 g of 4-amino-1H-pyrazole-3-carboxylic acid 2,4-dimethoxybenzylamide hydrochloride and 1.3 ml of diisopropylethylamine in 70 ml of THF is stirred for five minutes, and 1.2 g of 3-nitrobenzaldehyde and 0.85 g of magnesium sulfate are then added to this solution. The reaction medium is refluxed for one hour and, after cooling to 45° C., 74 g of sodium triacetoxyborohydride are added portionwise and the mixture is refluxed for a further three hours. Since not all the starting material has disappeared, after cooling to 45° C., 7.4 g of sodium triacetoxyborohydride are added portionwise, and the mixture is refluxed for a further two hours. After cooling the reaction medium to room temperature, it is poured into 350 ml of distilled water. The pale yellow milky solution thus obtained is brought to pH 8-9 by adding 60 ml of aqueous 2N sodium hydroxide solution. 250 ml of dichloromethane are added and, after separation of the phases by settling and then extraction of the aqueous phase with twice 150 ml of dichloromethane, the organic phases are combined, washed with 250 ml of saturated aqueous sodium chloride solution, dried over magnesium sulfate, filtered and concentrated to dryness under reduced pressure. 3.19 g of a tacky oil are obtained, which product is chromatographed on a column of silica (90 g of Merck cartridge silica with a particle size of 15 to 45 μm, column diameter 4.7 cm, 15 ml fractions, flow rate of 18 ml/min, eluent 70/30 ethyl acetate/cyclohexane—by volume). Fractions 34 to 110 are combined and evaporated to dryness under reduced pressure. 2.22 g of 4-[(3-nitrobenzyl)ethylamino]-1H-pyrazole-3-carboxamide are obtained in the form of a yellow foam. ([M+H]+): 453). RT: 4.02 min (Method A).

EXAMPLE 36

4-({3-[3-(2-chloro-5-trifluoromethylphenyl)ureido]benzyl}methyl-amino)-1H-pyrazole-3-carboxamide

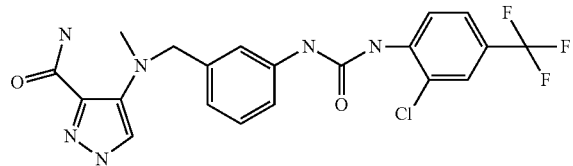 [SMILES: CN(Cc1cccc(NC(=O)Nc2ccc(C(F)(F)F)cc2Cl)c1)c1c[nH]nc1C(N)=O]

4-({3-[3-(2-Chloro-5-trifluoromethylphenyl)ureido]benzyl}methylamino)-1H-pyrazole-3-carboxamide is obtained by condensing 1-chloro-2-isocyanato-4-trifluoromethylbenzene with 4-[(3-aminobenzyl)methylamino]-1H-pyrazole-3-carboxamide according to the procedure described in Example 34.

([M+H]+): 467). RT: 3.81 min (Method A).

EXAMPLE 37

4-{3-[3-(4-trifluoromethylpyrid-2-yl)ureido]benzylamino}-1H-pyrazole-3-carboxamide

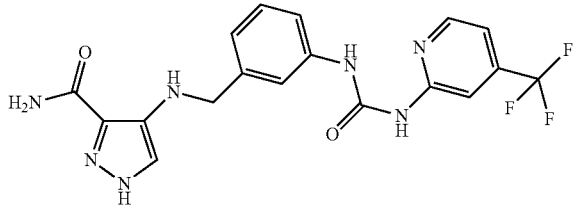 [SMILES: NC(=O)c1n[nH]cc1NCc1cccc(NC(=O)Nc2cc(C(F)(F)F)ccn2)c1]

88 μl of triethylamine and 0.18 g of phenyl (4-trifluoromethylpyrid-2-yl)carbamate are added at 20° C. to a solution of 0.12 g of 4-(3-aminobenzylamino)-1H-pyrazole-3-carboxamide in 5 ml of anhydrous THF. The reaction medium is heated in a microwave reactor for 20 minutes and, after cooling, is diluted with 25 ml of ethyl acetate. The organic phase is washed with twice 15 ml of distilled water and then separated out by settling of the phases, dried over magnesium sulfate and evaporated to dryness under reduced pressure. The residue obtained is chromatographed on a column of silica (15 g of Merck cartridge silica with a particle size of 15 to 45 μm, column diameter 2.2 cm, 3.5 ml fractions, flow rate of 7 ml/min, ethyl acetate eluent). Fractions 36 to 60 are combined and evaporated to dryness under reduced pressure. 0.06 g of 4-{3-[3-(4-trifluoromethylpyrid-2-yl)ureido]benzylamino}-1H-pyrazole-3-carboxamide is obtained in the form of a white solid. ([M+H]+): 420). RT: 0.78 min (Method D).

Phenyl (4-trifluoromethylpyrid-2-yl)carbamate is prepared in the following manner:

0.81 ml of pyridine is added to a solution of 2-amino-4-trifluoromethylpyridine in 65 ml of anhydrous tetrahydrofuran, the reaction mixture is cooled to 5° C., and 0.95 ml of phenyl chloroformate is then added at this temperature. After stirring for 2 hours at 5° C., the reaction mixture is allowed to warm to room temperature and is then poured into 20 ml of distilled water and maintained at a temperature of 20° C. 50 ml of ethyl acetate are then added, the phases are separated by settling and the aqueous phase is extracted twice with 20 ml of ethyl acetate. The organic phases are combined, dried over magnesium sulfate, filtered and then evaporated to dryness. The solid obtained is triturated in 10 ml of diisopropyl ether. 1.07 g of phenyl 4-trifluoromethylpyrid-2-yl)carbamate are obtained in the form of a white solid melting at 161° C. ([M+H]): 281). Rt: 4.30 MIN (Method A).

EXAMPLE 38

4-{3-[3-(4-methoxypyrid-2-yl)ureido]benzylamino}-1H-pyrazole-3-carboxamide

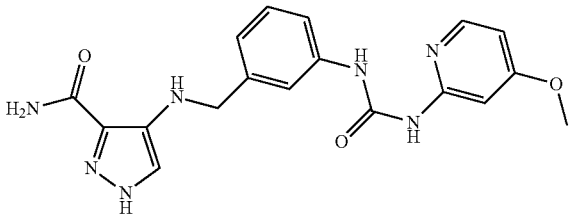 [SMILES: COc1ccnc(NC(=O)Nc2cccc(CNc3c[nH]nc3C(N)=O)c2)c1]

EXAMPLE 39

(RS)-4-(1-{3-[3-(2-chloro-4-trifluoromethylphenyl)ureido]phenyl}ethyl-amino)-1H-pyrazole-3-carboxamide trifluoroacetate

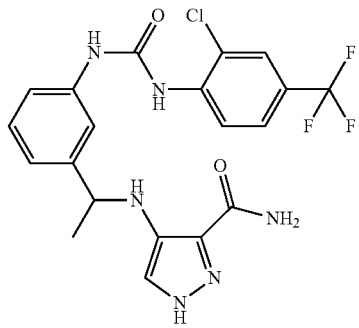 [SMILES: CC(Nc1c[nH]nc1C(N)=O)c1cccc(NC(=O)Nc2ccc(C(F)(F)F)cc2Cl)c1]

Examples 40 to 58, described in Table A below, are obtained or could be obtained by condensing the corresponding isocyanates with 4-[(3-aminobenzyl)amino]-1H-pyrazole-3-carboxamide according to the procedure described in Example 34.

TABLE A

| Example No. | Structure | [M + H]+ (Method D) | RT (min) |
|---|---|---|---|
| 40 | 4-[[3-[[(3-chloro-4-fluorophenyl)carbamoyl]amino]phenyl]methylamino]-1H-pyrazole-3-carboxamide | 403 | 0.78 |
| 41 | 4-[[3-[[(3,4-dichlorophenyl)carbamoyl]amino]phenyl]methylamino]-1H-pyrazole-3-carboxamide | 419 | 0.91 |
| 42 | 4-[[3-[[[3-chloro-5-(trifluoromethyl)phenyl]carbamoyl]amino]phenyl]methylamino]-1H-pyrazole-3-carboxamide | 453 | 0.96 |
| 43 | 4-[[3-[[[4-fluoro-3-(trimethylsilyl)phenyl]carbamoyl]amino]phenyl]methylamino]-1H-pyrazole-3-carboxamide | 442 | n.d. |
| 44 | 4-[[3-[[[3-(trifluoromethoxy)phenyl]carbamoyl]amino]phenyl]methylamino]-1H-pyrazole-3-carboxamide | 435 | n.d. |
| 45 | 4-[[3-[[[4-chloro-3-(trifluoromethyl)phenyl]carbamoyl]amino]phenyl]methylamino]-1H-pyrazole-3-carboxamide | 453 | 0.92 |
| 46 | 4-[[3-[[[2-chloro-5-(trifluoromethyl)phenyl]carbamoyl]amino]phenyl]methylamino]-1H-pyrazole-3-carboxamide | 454 | n.d. |

TABLE A-continued

| Example No. | Structure | [M + H]+ (Method D) | RT (min) |
|---|---|---|---|
| 47 | pyrazole-3-carboxamide-4-NH-CH2-(3-phenyl)-NH-C(O)-NH-(3-(SCF3)phenyl) | 451 | 0.91 |
| 48 | pyrazole-3-carboxamide-4-NH-CH2-(3-phenyl)-NH-C(O)-NH-(3-isopropylphenyl) | 393 | 0.86 |
| 49 | pyrazole-3-carboxamide-4-NH-CH2-(3-phenyl)-NH-C(O)-NH-(3-isopropyl-4-fluorophenyl) | 411 | n.d. |
| 50 | pyrazole-3-carboxamide-4-NH-CH2-(3-phenyl)-NH-C(O)-NH-(3-SF5-phenyl) | 477 | n.d. |
| 51 | pyrazole-3-carboxamide-4-NH-CH2-(3-phenyl)-NH-C(O)-NH-(2-methoxy-5-tert-butylphenyl) | 437 | 0.96 |
| 52 | pyrazole-3-carboxamide-4-NH-CH2-(3-phenyl)-NH-C(O)-NH-(4-isopropylphenyl) | 393 | 0.86 |
| 53 | pyrazole-3-carboxamide-4-NH-CH2-(3-phenyl)-NH-C(O)-NH-(2-chloro-4-isopropylphenyl) | 428 | n.d. |

TABLE A-continued

| Example No. | Structure | [M + H]+ (Method D) | RT (min) |
|---|---|---|---|
| 54 | 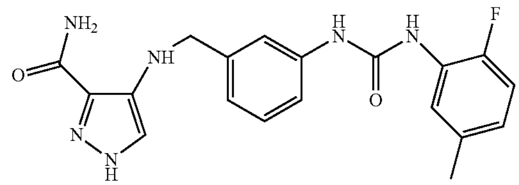 [SMILES: Cc1ccc(F)c(NC(=O)Nc2cccc(CNc3c[nH]nc3C(N)=O)c2)c1] | 383 | 0.74 |
| 55 | 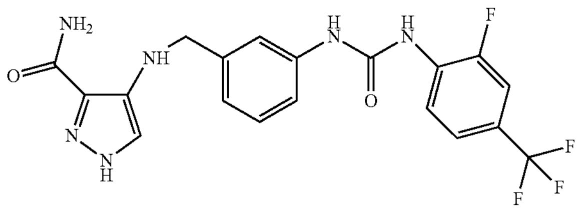 [SMILES: NC(=O)c1n[nH]cc1NCc1cccc(NC(=O)Nc2ccc(C(F)(F)F)cc2F)c1] | 437 | 0.89 |
| 56 | 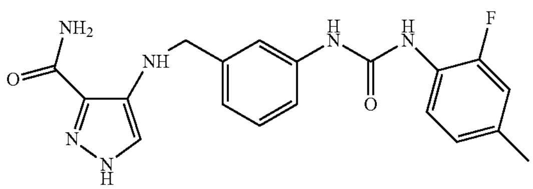 [SMILES: Cc1ccc(NC(=O)Nc2cccc(CNc3c[nH]nc3C(N)=O)c2)c(F)c1] | 383 | 0.74 |
| 57 | 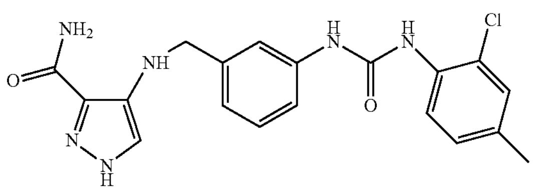 [SMILES: Cc1ccc(NC(=O)Nc2cccc(CNc3c[nH]nc3C(N)=O)c2)c(Cl)c1] | 399 | 0.8 |
| 58 | | 399 | 0.81 | n.d. not determined

Determination of the Activity of the Compounds—Experimental Protocols

1. KDR

The inhibitory effect of the compounds is determined in an in vitro test of phosphorylation of substrate with the enzyme KDR via a scintillation technique (96-well plate, NEN).

The cytoplasmic domain of the human KDR enzyme was cloned in the form of a GST fusion in the pFastBac baculovirus expression vector. The protein was expressed in the SF21 cells and purified to about 60% homogeneity.

The KDR kinase activity is measured in 20 mM MOPS, 10 mM $MgCl_2$, 10 mM $MnCl_2$, 1 mM DTT, 2.5 mM EGTA, 10 mM b-glycerophosphate, pH=7.2, in the presence of 10 mM $MgCl_2$, 100 μm $Na_3VO_4$, 1 mM NaF. 10 μl of the compound are added to 70 μl of kinase buffer containing 100 ng of KDR enzyme at 4° C. The reaction is initiated by adding 20 μl of solution containing 2 μg of substrate (SH2-SH3 fragment of PLCγ expressed in the form of a GST fusion protein), 2 μCi of $γ^{33}P[ATP]$ and 2 μm of cold ATP. After incubation for 1 hour at 37° C., the reaction is stopped by adding 1 volume (100 μl) of 200 mM EDTA. The incubation buffer is removed, and the wells are washed three times with 300 μl of PBS. The radioactivity in each well is measured using a Top Count NXT radioactivity counter (Packard).

The background noise is determined by measuring the radioactivity in four different wells containing radioactive ATP and the substrate alone.

A total activity control is measured in four different wells containing all the reagents ($γ^{33}P$-[ATP], KDR and substrate PLCγ), but in the absence of compound.

The inhibition of the KDR activity with the compound of the invention is expressed as a percentage of inhibition of the control activity determined in the absence of compound.

Compound SU5614 (Calbiochem) (1 μM) is included in each plate as an inhibition control.

2. Tie2

The coding sequence of human Tie2 corresponding to the amino acids of the intracellular domain 776-1124 was generated by PCR using the cDNA isolated from a human placenta as a model. This sequence was introduced into a pFastBacGT baculovirus expression vector in the form of a GST fusion protein.

The inhibitory effect of the molecules is determined in a test of phosphorylation of PLC with Tie2 in the presence of GST-Tie2 purified to about 80% homogeneity. The substrate is composed of the SH2-SH3 fragments of PLC expressed in the form of a GST fusion protein.

The kinase activity of Tie2 is measured in a MOPS 20 mM pH 7.2 buffer, containing 10 mM $MgCl_2$, 10 mM $MnCl_2$, 1 mM DTT, 10 mM of glycerophosphate. In a 96-well Flash-Plate plate maintained on ice, a reaction mixture is deposited, composed of 70 μL of kinase buffer containing 100 ng of enzyme GST-Tie2 per well. Next, 10 μL of the test molecule diluted in DMSO to a maximum concentration of 10% are added. For a given concentration, each measurement is performed four times. The reaction is initiated by adding 20 μl of solution containing 2 μg of GST-PLC, 2 μm of cold ATP and 1 μCi of $\delta^{33}P[ATP]$. After incubation for one hour at 37° C., the reaction is stopped by adding 1 volume (100 μl) of 200 mM EDTA. After removal of the incubation buffer, the wells are washed three times with 300 μL of PBS. The radioactivity is measured on a MicroBeta 1450 Wallac.

The inhibition of the Tie2 activity is calculated and expressed as a percentage of inhibition relative to the control activity determined in the absence of compound.

Results:

The compounds of the examples of the invention have a concentration that inhibits 50% of the kinase activity generally of between 0.1 nM and 2 μM on KDR and/or Tie2, preferably between 0.1 nM and 500 nM and more preferentially between 0.1 nM and 50 nM. The values in Table 1 below are given as illustrations.

TABLE 1

| Example | KDR | Tie2 |
|---|---|---|
| 2a | 8 | 20 |
| 7 | 4.5 | 72.7 |
| 9 | 21.8 | 4510.4 |
| 13 | 11.8 | 1461.9 |
| 32 | 64.1 | 1000.8 |

What is claimed is:

1. A compound of formula (I):

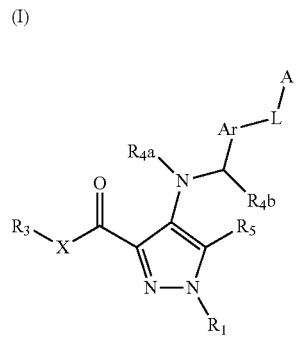

(I)

wherein:
1) A and Ar are independently selected from the group consisting of: aryl, and substituted aryl,
2) L is O—CO—NH;
3) $R_1$ is selected from the group consisting of: H, $R_6$, $COR_6$, $SO_2R_6$, in which $R_6$ is chosen from H, $OR_7$, $NR_8R_9$, alkyl, cycloalkyl, heterocyclyl, substituted heterocyclyl, aryl, substituted aryl, heteroaryl and substituted heteroaryl, in which $R_7$ is chosen from H, phenyl and alkyl, and in which $R_8$ and $R_9$ are independently selected from the group consisting of H, alkyl, cycloalkyl, heterocyclyl, substituted heterocyclyl, aryl, substituted aryl, heteroaryl and substituted heteroaryl, or alternatively $R_8$ and $R_9$ are linked together to form a saturated 5- to 8-membered ring containing from 0 to 3 heteroatoms chosen from O, S and N;
4) X is selected from the group consisting of: O and NH;
5) $R_3$ is selected from the group consisting of H, alkyl, substituted alkyl, cycloalkyl, substituted cycloalkyl;
6) $R_{4a}$ is selected from the group consisting of: H and (C1-C4)alkyl;
7) $R_{4b}$ is selected from the group consisting of: H and (C1-C4)alkyl;
8) $R_5$ is selected from the group consisting of H, halogen, $R_{10}$, CN, $O(R_{10})$, $OC(O)(R_{10})$, $OC(O)N(R_{10})(R_{11})$, $OS(O_2)(R_{10})$, $N(R_{10})(R_{11})$, $N=C(R_{10})(R_{11})$, $N(R_{10})C(O)(R_{11})$, $N(R_{10})C(O)O(R_{11})$, $N(R_{12})C(O)N(R_{10})(R_{11})$, $N(R_{12})C(S)N(R_{10})(R_{11})$, $N(R_{10})S(O_2)(R_{11})$, $C(O)(R_{10})$, $C(O)O(R_{10})$, $C(O)N(R_{10})(R_{11})$, $C(=N(R_{11}))(R_{10})$, $C(=N(OR_{11}))(R_{10})$, $S(R_{10})$, $S(O)(R_{10})$, $S(O_2)(R_{10})$, $S(O_2)O(R_{10})$, $S(O_2)N(R_{10})(R_{11})$; in which each $R_{10}$, $R_{11}$, $R_{12}$ is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl and substituted heterocyclyl.

2. The compound according to claim 1, wherein $R_{4a}$ and $R_{4b}$ are H.

3. The compound according to claim 1, wherein $R_{4a}$ is H and $R_{4b}$ is (C1-C4)alkyl.

4. The compound according to claim 1, wherein $R_{4a}$ is (C1-C4)alkyl and $R_{4b}$ is H.

5. The compound according to claim 1, wherein $R_1$ is H.

6. The compound according to claim 1, wherein $R_3$ is H and X is NH.

7. The compound according to claim 1, wherein $R_3$ is methyl and X is O.

8. The compound according to claim 1, wherein $R_5$ is H.

9. The compound according to claim 1, wherein Ar-L-A is:

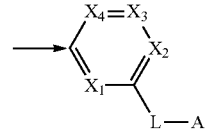

in which each $X_1$, $X_2$, $X_3$ and $X_4$ is independently chosen from C—$R'_5$, in which $R'_5$ has the same definition as $R_5$.

10. The compound according to claim 9, characterized in that $R'_5$ is selected from the group consisting of H, F, Cl, methyl, $NH_2$, $OCF_3$ and $CONH_2$.

11. The compound according to claim 9, characterized in that A is chosen from phenyl, optionally substituted.

12. The compound according to claim 1, wherein A is substituted with one or more substituents selected from the group consisting of: H, F, Cl, Br, I, OH, SH, $SO_3M$, COOM, COO-alkyl, $CON(R_{14})(R_{15})$, CN, $NO_2$, $N(R_{14})CO(R_{15})$, $N(R_{14})(R_{15})$, alkyl, haloalkyl, alkyl-OH, alkyl-$N(R_{14})(R_{15})$, alkyl($R_{16}$), alkyl-COOM, alkyl-$SO_3M$, cycloalkyl, alkylene, alkynyl, aryl, heteroaryl, O-alkyl, O-aryl, O-heteroaryl, S-alkyl, S-aryl and S-heteroaryl, each being optionally substituted with a substituent chosen from alkyl, halogen, O-alkyl and N($R_{14}$)($R_{15}$); in which $R_{14}$ and $R_{15}$ are independently chosen from H, alkyl, alkyl-OH, haloalkyl, alkyl-NH$_2$, alkyl-COOM and alkyl-SO$_3$M; in which, when $R_{14}$ and $R_{15}$ are simultaneously other than H, may be bonded to form a 5- to 7-membered ring comprising from 0 to 3 heteroatoms chosen from 0, N and S; in which M is H or a cation of an alkali metal chosen from Li, Na and K; and in which $R_{16}$ is H or an optionally substituted non-aromatic heterocycle, containing from 2 to 7 carbon atoms, and 1 to 3 heteroatoms chosen from N, O and S; when A is disubstituted, the two substituents may be linked together to form a 5- to 7-membered ring containing from 0 to 3 heteroatoms chosen from N, O and S.

13. The compound according to claim 1, wherein A is substituted with one or more substituents selected from the group consisting of SiMe$_3$, S—CHF$_3$, SF$_5$, H, F, Cl, Br, I, OH, SH, SO$_3$M, COOM, COO-alkyl, CON($R_{14}$)($R_{15}$), CN, NO$_2$, N($R_{14}$)CO($R_{15}$), N($R_{14}$)($R_{15}$), alkyl, haloalkyl, alkyl-OH, alkyl-N($R_{14}$)($R_{15}$), alkyl($R_{16}$), alkyl-COOM, alkyl-SO$_3$M, cycloalkyl, alkylene, alkynyl, aryl, heteroaryl, O-alkyl, O-aryl, O-heteroaryl, S-alkyl, S-aryl and S-heteroaryl, each being optionally substituted with a substituent chosen from alkyl, halogen, O-alkyl and N($R_{14}$)($R_{15}$); wherein $R_{14}$ and $R_{15}$ are independently chosen from H, alkyl, alkyl-OH, haloalkyl, alkyl-NH$_2$, alkyl-COOM and alkyl-SO$_3$M; wherein, when $R_{14}$ and $R_{15}$ are simultaneously other than H, they may be bonded to form a 5- to 7-membered ring comprising from 0 to 3 heteroatoms chosen from 0, N and S; wherein M is H or a cation of an alkali metal chosen from Li, Na and K; and wherein $R_{16}$ is H or an optionally substituted non-aromatic heterocycle, containing from 2 to 7 carbon atoms, and 1 to 3 heteroatoms chosen from N, O and S; when A is disubstituted, the two substituents may be linked together to form a 5- to 7-membered ring containing from 0 to 3 heteroatoms chosen from N, O and S; or a salt thereof.

14. The compound according to claim 1, which is:
4-{[3-phenyl]carbamoyl}oxy)benzyl]amino-1H-pyrazole-3-carboxamide trifluoroacetate.

15. The compound according to claim 1, wherein it is:
1) in non-chiral form, or
2) in racemic form, or
3) enriched in one stereoisomer, or
4) enriched in one enantiomer;
and in that it is optionally salified.

16. A pharmaceutical composition comprising a product according to claim 1, or a pharmaceutically acceptable salt thereof, in combination with a pharmaceutically acceptable excipient.

17. A pharmaceutical composition comprising a product according to claim 14, or a pharmaceutically acceptable salt thereof, in combination with a pharmaceutically acceptable excipient.

18. A method for inhibiting one or more reactions catalysed by a kinase, comprising contacting said kinase with a compound according to claim 1 or a pharmaceutically acceptable salt thereof.

19. The method of claim 18, wherein the kinase is chosen from KDR and Tie2.

20. A method for treating a patient having a pathological condition in which receptors of KDR are involved, comprising administering to said patient a therapeutically effective amount of a compound according to claim 1 or a pharmaceutically acceptable salt thereof.

21. The method according to claim 20, wherein the pathological condition is cancer.

22. A process for preparing the compounds of formula (Ib):

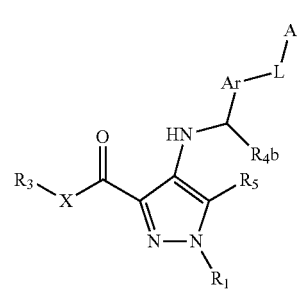

(Ib)

in which $R_1$, $R_3$, $R_{4b}$, $R_5$, X, Ar, L and A are as defined in claim 1, and $R_{4a}$ is H, characterized in that a compound of formula (II):

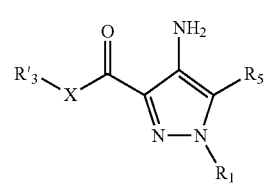

(II)

in which R'$_3$ is $R_3$ or a precursor of $R_3$, and X, $R_1$, $R_3$ and $R_5$ are as defined in claim 1, reacts with a compound of formula (III):

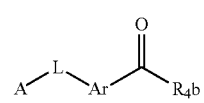

(III)

in which $R_{4b}$, Ar, L and A are as defined in claim 1, to give the compound of formula (Ib).

23. A process for preparing the compounds of formula (I):

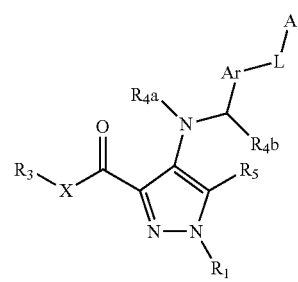

(I)

in which $R_1$, $R_3$, $R_{4a}$, $R_{4b}$, $R_5$, X, Ar and A are as defined in claim 1, and L is NHCONH, characterized in that a compound of formula (VIII):

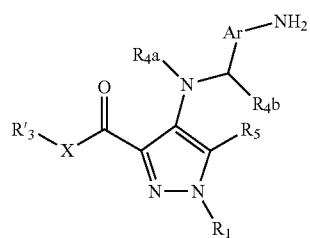
(VIII)
in which R'$_3$ is R$_3$ or a precursor of R$_3$, and X, Ar, R$_1$, R$_3$, R$_{4a}$, R$_{4b}$ and R$_5$ are as defined in claim 1, reacts with a compound of formula (VII):
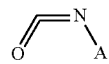
(VII)
in which A is as defined in claim 1, to give the compound of formula (I')
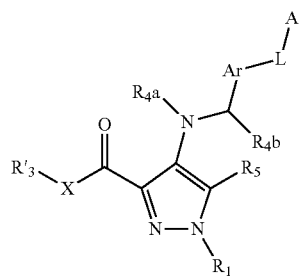
(I')
in which the precursor R'$_3$ is transformed into R$_3$ in order to obtain the compound of formula (I).
* * * * *